United States Patent [19]

Kamboj et al.

[11] Patent Number: 5,616,481
[45] Date of Patent: Apr. 1, 1997

[54] KAINATE-BINDING HUMAN CNS RECEPTORS OF THE EAA1 FAMILY

[75] Inventors: Rajender Kamboj, Mississauga; Stephen L. Nutt, Etobicoke; Lee Shekter, Toronto; Michael A. Wosnick, Thornhill, all of Canada

[73] Assignee: Allelix Biopharmaceuticals Inc., Mississauga, Canada

[21] Appl. No.: 416,523

[22] Filed: Apr. 3, 1995

Related U.S. Application Data

[60] Continuation of Ser. No. 91,441, Jul. 15, 1993, abandoned, which is a division of Ser. No. 750,090, Aug. 26, 1991, abandoned.

[51] Int. Cl.$^6$ ............... C07K 14/705; C12N 5/10; C12N 15/09; C12N 15/12
[52] U.S. Cl. ............... 435/172.3; 435/317.1; 436/501; 530/350; 536/23.5
[58] Field of Search ............... 435/69.1, 172.3, 435/240.2, 7.21, 4, 317.1; 530/350; 536/235; 436/501

[56] References Cited

FOREIGN PATENT DOCUMENTS

WO91/06648 of 0000 WIPO.

OTHER PUBLICATIONS

Egebjerg, J. et al. *Nature* 351:745–748 (1991).
Wada, K. et al. *Nature* 342:684–689 (1989).
Werner, P. et al. *Nature* 351:742–744 (1991).
Hollmann et al, Nature 1989 342:643.
Keinanen et al, Science 1990 249:556.
Boulter et al, Science 1990:249:1033.
Bettler et al, Neuron 1990 5:583.
Sommer et al, Science 1990 249:1580.
Monyer et al, Neuron 1991 6:799.
Nakanishi et al, Neuron 1990 5:569.
Hollmann et al, Science 1991 252:851.
Verdoom et al, Science 1991 252:1715.
Gregor et al, Nature 1989 342:689.
Barnett et al, Nucleic Acids Res. 1990 18(10):3094.
Suggs, S.V. et al, *PNAS* 78(11):6613–6617, (1981).

*Primary Examiner*—Dian C. Jacobson

[57] ABSTRACT

Neurotransmission by excitatory amino acids (EAAs) such as glutamate is mediated via membrane-bound surface receptors. DNA coding for one family of these receptors, of the kainate binding type of EAA receptors, has now been isolated and the receptor protein characterized. Herein described are recombinant cell lines which produce the EAA receptor as a heterologous membrane-bound product. Also described are related aspects of the invention, which are of commercial significance. Included is use of the cell lines as a tool for discovery of compounds which modulate EAA receptor stimulation.

15 Claims, 14 Drawing Sheets

FIG. 1(A)

```
(Linear) MAP of : HumEAA1a
      GAATTCCCTGAGTGCCTACTATGTGCCAGCCTGTGCTAGGCACTGAGGACACAGGTGGAA
   1 ---------+---------+---------+---------+---------+---------+ 60
      CTTAAGGGACTCACGGATGATACACGGTCGGACACGATCCGTGACTCCTGTGTCCACCTT
                                    HphI
                                     |
      AAGCCCGAATTGCTCCCTGCTCTCCTGGCGCTCATCACCCCGGAGAGTTATGTCATGCCC
  61 ---------+---------+---------+---------+---------+---------+ 120
      TTCGGGCTTAACGAGGGACGAGAGGACCGCGAGTAGTGGGGCCTCTCAATACAGTACGGG AGGCCAGCAGGGGGCTCCATGAGGATTCATAGAAGATGCCCCGCGTCTCGGCGCCTTTGG
 121 ---------+---------+---------+---------+---------+---------+ 180
      TCCGGTCGTCCCCCGAGGTACTCCTAAGTATCTTCTACGGGGCGCAGAGCCGCGGAAACC
                                         M   P   R   V   S   A   P   L   V
                                        -20                 -15
                                       PstI
                                        |
      TGCTGCTTCCTGCGTGGCTCGTGATGGTCGCCTGCAGCCCGCACTCCTTGAGGATCGCTG
 181 ---------+---------+---------+---------+---------+---------+ 240
      ACGACGAAGGACGCACCGAGCACTACCAGCGGACGTCGGGCGTGAGGAACTCCTAGCGAC
       L   L   P   A   W   L   V   M   V   A   C  S₁  P   H   S   L   R   I   A   A 9
          -10                  -5                  |_Mature N-terminal NcoI                          HphI
            |                             |
      CTATCTTGGACGACCCCATGGAGTGCAGCAGAGGGGAGCGGCTCTCCATCACCCTGGCCA
 241 ---------+---------+---------+---------+---------+---------+ 300
      GATAGAACCTGCTGGGGTACCTCACGTCGTCTCCCCTCGCCGAGAGGTAGTGGGACCGGT
  10  I   L   D   D   P   M   E   C   S   R   G   E   R   L   S   I   T   L   A  K 29

AGAACCGCATCAACCGCGCTCCTGAGAGGCTGGGCAAGGCCAAGGTCGAAGTGGACATCT
 301 ---------+---------+---------+---------+---------+---------+ 360
      TCTTGGCGTAGTTGGCGCGAGGACTCTCCGACCCGTTCCGGTTCCAGCTTCACCTGTAGA
  30  N   R   I   N   R   A   P   E   R   L   G   K   A   K   V   E   D   I   F
                                                          PstI
                                                           |
      TTGAGCTTCTCAGAGACAGCGAGTACGAGACTGCAGAAACCATGTGTCAGATCCTCCCCA
 361 ---------+---------+---------+---------+---------+---------+ 420
      AACTCGAAGAGTCTCTGTCGCTCATGCTCTGACGTCTTTGGTACACAGTCTAGGAGGGGT
  50  E   L   L   R   D   S   E   Y   E   T   A   E   T   M   C   Q   I   L   P  K 49

AGGGGGTGGTCGCTGTCCTCGGACCATCGTCCAGCCCAGCCTCCAGCTCCATCATCAGCA
 421 ---------+---------+---------+---------+---------+---------+ 480
      TCCCCCACCAGCGACAGGAGCCTGGTAGCAGGTCGGGTCGGAGGTCGAGGTAGTAGTCGT
  70  G   V   V   A   V   L   G   P   S   S   S   P   A   S   S   S   I   I   S  N 69
```

FIG. 1(B)

```
     ACATCTGTGGAGAGAAGGAGGTCCCTCACTTCAAAGTGGCCCCAGAGGAGTTCGTCAAGT
481 ---------+---------+---------+---------+---------+---------+ 540
     TGTAGACACCTCTCTTCCTCCAGGGAGTGAAGTTTCACCGGGGTCTCCTCAAGCAGTTCA
   90 I  C  G  E  K  E  V  P  H  F  K  V  A  P  E  E  F  V  K  F 109

TCCAGTTCCAGAGATTCACAACCCTGAACCTCCACCCCAGCAACACTGACATCAGCGTGG
541 ---------+---------+---------+---------+---------+---------+ 600
     AGGTCAAGGTCTCTAAGTGTTGGGACTTGGAGGTGGGGTCGTTGTGACTGTAGTCGCACC
  110 Q  F  Q  R  F  T  T  L  N  L  H  P  S  N  T  D  I  S  V  A 129
                  BamHI        XmnI
                    |            |
     CTGTAGCTGGGATCCTGAACTTCTTCAACTGCACCACCGCCTGCCTCATCTGTGCCAAAG
601 ---------+---------+---------+---------+---------+---------+ 660
     GACATCGACCCTAGGACTTGAAGAAGTTGACGTGGTGGCGGACGGAGTAGACACGGTTTC
  130 V  A  G  I  L  N  F  F  N  C  T  T  A  C  L  I  C  A  K  A 149

CAGAATGCCTTTTAAACCTAGAGAAGCTGCTCCGGCAATTCCTTATCTCCAAGGACACGC
661 ---------+---------+---------+---------+---------+---------+ 720
     GTCTTACGGAAAATTTGGATCTCTTCGACGAGGCCGTTAAGGAATAGAGGTTCCTGTGCG
  150 E  C  L  L  N  L  E  K  L  L  R  Q  F  L  I  S  K  D  T  L 169

TGTCCGTCCGCATGCTGGATGACACCCGGGACCCCACCCCGCTCCTCAAGGAGATCCGGG
721 ---------+---------+---------+---------+---------+---------+ 780
     ACAGGCAGGCGTACGACCTACTGTGGGCCCTGGGGTGGGGCGAGGAGTTCCTCTAGGCCC
  170 S  V  R  M  L  D  D  T  R  D  P  T  P  L  L  K  E  I  R  D 189

ACGACAAGACCGCCACCATCATCATCCACGCCAACGCCTCCATGTCCCACACCATCCTCC
781 ---------+---------+---------+---------+---------+---------+ 840
     TGCTGTTCTGGCGGTGGTAGTAGTAGGTGCGGTTGCGGAGGTACAGGGTGTGGTAGGAGG
  190 D  K  T  A  T  I  I  I  H  A  N  A  S  M  S  H  T  I  L  L 209

TGAAGGCAGCCGAACTTGGGATGGTGTCAGCCTATTACACATACATCTTCACTAATCTGG
841 ---------+---------+---------+---------+---------+---------+ 900
     ACTTCCGTCGGCTTGAACCCTACCACAGTCGGATAATGTGTATGTAGAAGTGATTAGACC
  210 K  A  A  E  L  G  M  V  S  A  Y  Y  T  Y  I  F  T  N  L  E 229

AGTTCTCACTCCAGAGAACGGACAGCCTTGTGGATGATCGTGTCAACATCCTGGGATTTT
901 ---------+---------+---------+---------+---------+---------+ 960
     TCAAGAGTGAGGTCTCTTGCCTGTCGGAACACCTACTAGCACAGTTGTAGGACCCTAAAA
  230 F  S  L  Q  R  T  D  S  L  V  D  D  R  V  N  I  L  G  F  S 249

CCATTTTCAACCAATCCCATGCTTTCTTCCAAGAGTTTGCCCAGAGCCTCAACCAGTCCT
961 ---------+---------+---------+---------+---------+---------+ 1020
     GGTAAAAGTTGGTTAGGGTACGAAAGAAGGTTCTCAAACGGGTCTCGGAGTTGGTCAGGA
  250 I  F  N  Q  S  H  A  F  F  Q  E  F  A  Q  S  L  N  Q  S  W 269
```

FIG. 1(C)

```
           GGCAGGAGAACTGTGACCATGTGCCCTTCACTGGGCCTGCGCTCTCCTCGGCCCTGCTGT
    1021 ---------+---------+---------+---------+---------+---------+ 1080
           CCGTCCTCTTGACACTGGTACACGGGAAGTGACCCGGACGCGAGAGGAGCCGGGACGACA
       270 Q  E  N  C  D  H  V  P  F  T  G  P  A  L  S  S  A  L  L  F 289
                                           HphI
           TTGATGCTGTCTATGCTGTGGTGACTGCGGTGCAGGAACTGAACCGGAGCCAAGAGATCG
    1081 ---------+---------+---------+---------+---------+---------+ 1140
           AACTACGACAGATACGACACCACTGACGCCACGTCCTTGACTTGGCCTCGGTTCTCTAGC
       290 D  A  V  Y  A  V  V  T  A  V  Q  E  L  N  R  S  Q  E  I  G 309
           GCGTGAAGCCCTTGTCCTGCGGCTCGGCCCAGATCTGGCAGCACGGCACCAGCCTCATGA
    1141 ---------+---------+---------+---------+---------+---------+ 1200
           CGCACTTCGGGAACAGGACGCCGAGCCGGGTCTAGACCGTCGTGCCGTGGTCGGAGTACT
       310 V  K  P  L  S  C  G  S  A  Q  I  W  Q  H  G  T  S  L  M  N 329
                                                         EcoRI
           ACTACCTGCGCATGGTAGAATTGGAAGGTCTTACCGGCCACATTGAATTCAACAGCAAAG
    1201 ---------+---------+---------+---------+---------+---------+ 1260
           TGATGGACGCGTACCATCTTAACCTTCCAGAATGGCCGGTGTAACTTAAGTTGTCGTTTC
       330 Y  L  R  M  V  E  L  E  G  L  T  G  H  I  E  F  N  S  K  G 349
           GCCAGAGGTCCAACTACGCTTTGAAAATCTTACAGTTCACAAGGAATGGTTTTCGGCAGA
    1261 ---------+---------+---------+---------+---------+---------+ 1320
           CGGTCTCCAGGTTGATGCGAAACTTTTAGAATGTCAAGTGTTCCTTACCAAAAGCCGTCT
       350 Q  R  S  N  Y  A  L  K  I  L  Q  F  T  R  N  G  F  R  Q  I 369
           TCGGCCAGTGGCACGTGGCAGAGGGCCTCAGCATGGACAGCCACCTCTATGCCTCCAACA
    1321 ---------+---------+---------+---------+---------+---------+ 1380
           AGCCGGTCACCGTGCACCGTCTCCCGGAGTCGTACCTGTCGGTGGAGATACGGAGGTTGT
       370 G  Q  W  H  V  A  E  G  L  S  M  D  S  H  L  Y  A  S  N  I 389
                                            HphI
           TCTCGGACACTCTCTTCAACACCACCCTGGTCGTCACCACCATCCTGGAAAACCCATATT
    1381 ---------+---------+---------+---------+---------+---------+ 1440
           AGAGCCTGTGAGAGAAGTTGTGGTGGGACCAGCAGTGGTGGTAGGACCTTTTGGGTATAA
       390 S  D  T  L  F  N  T  T  L  V  V  T  T  I  L  E  N  P  Y  L 409
           TAATGCTGAAGGGGAACCACCAGGAGATGGAAGGCAATGACCGCTACGAGGGCTTCTGTG
    1441 ---------+---------+---------+---------+---------+---------+ 1500
           ATTACGACTTCCCCTTGGTGGTCCTCTACCTTCCGTTACTGGCGATGCTCCCGAAGACAC
       410 M  L  K  G  N  H  Q  E  M  E  G  N  D  R  Y  E  G  F  C  V 429
           TGGACATGCTCAAGGAGCTGGCAGAGATCCTCCGATTCAACTACAAGATCCGCCTGGTTG
    1501 ---------+---------+---------+---------+---------+---------+ 1560
           ACCTGTACGAGTTCCTCGACCGTCTCTAGGAGGCTAAGTTGATGTTCTAGGCGGACCAAC
       430 D  M  L  K  E  L  A  E  I  L  R  F  N  Y  K  I  R  L  V  G 449
```

FIG. 1(D)

```
         GGGATGGCGTGTACGGCGTTCCCGAGGCCAACGGCACCTGGACGGGAATGGTCGGGGAGC
1561   ---------+---------+---------+---------+---------+---------+ 1620
         CCCTACCGCACATGCCGCAAGGGCTCCGGTTGCCGTGGACCTGCCCTTACCAGCCCCTCG
     450 D  G  V  Y  G  V  P  E  A  N  G  T  W  T  G  M  V  G  E  L 469
                                   HphI
                                    |
         TGATCGCTAGGAAAGCAGATCTGGCTGTGGCAGGCCTCACCATTACAGCTGAACGGGAGA
1621   ---------+---------+---------+---------+---------+---------+ 1680
         ACTAGCGATCCTTTCGTCTAGACCGACACCGTCCGGAGTGGTAATGTCGACTTGCCCTCT
     470 I  A  R  K  A  D  L  A  V  A  G  L  T  I  T  A  E  R  E  K 489
                       HphI
                        |
         AGGTGATTGATTTCTCTAAGCCATTCATGACTCTGGGAATTAGCATTCTTTACCGCATTC
1681   ---------+---------+---------+---------+---------+---------+ 1740
         TCCACTAACTAAAGAGATTCGGTAAGTACTGAGACCCTTAATCGTAAGAAATGGCGTAAG
     490 V  I  D  F  S  K  P  F  M  T  L  G  I  S  I  L  Y  R  I  H 509
         ATATGGACGCAAACCCGGCTATTTCTCCTTCCTGGACCCATTTTCTCCGGGCGTCTGGC
1741   ---------+---------+---------+---------+---------+---------+ 1800
         TATACCCTGCGTTTGGGCCGATAAAGAGGAAGGACCTGGGTAAAAGAGGCCCGCAGACCG
     510 M  G  R  K  P  G  Y  F  S  F  L  D  P  F  S  P  G  V  W  L 529
         TCTTCATGCTTCTAGCCTATCTGGCCGTCAGCTGTGTCCTCTTCCTGGTGGCTCGGTTGA
1801   ---------+---------+---------+---------+---------+---------+ 1860
         AGAAGTACGAAGATCGGATAGACCGGCAGTCGACACAGGAGAAGGACCACCGAGCCAACT
     530 F  M  L  L  A  Y  L  A  V  S  C  V  L  F  L  V  A  R  L  T 549
         CGCCCTACGAGTGGTACAGCCCACACCCATGTGCCCAGGGCCGGTGCAACCTCCTGGTGA
1861   ---------+---------+---------+---------+---------+---------+ 1920
         GCGGGATGCTCACCATGTCGGGTGTGGGTACACGGGTCCCGGCCACGTTGGAGGACCACT
     550 P  Y  E  W  Y  S  P  H  P  C  A  Q  G  R  C  N  L  L  V  N 569
                   HphI
                    |
         ACCAGTACTCCCTGGGCAACAGCCTCTGGTTTCCGGTCGGGGGGTTCATGCAGCAGGGCT
1921   ---------+---------+---------+---------+---------+---------+ 1980
         TGGTCATGAGGGACCCGTTGTCGGAGACCAAAGGCCAGCCCCCAAGTACGTCGTCCCGA
     570 Q  Y  S  L  G  N  S  L  W  F  P  V  G  G  F  M  Q  Q  G  S 589
         CCACCATCGCCCCTCGCGCCTTATCCACCCGCTGTGTCAGTGGCGTCTGGTGGGCATTCA
1981   ---------+---------+---------+---------+---------+---------+ 2040
         GGTGGTAGCGGGGAGCGCGGAATAGGTGGGCGACACAGTCACCGCAGACCACCCGTAAGT
     590 T  I  A  P  R  A  L  S  T  R  C  V  S  G  V  W  W  A  F  T 609
         CGCTGATCATCATCTCATCCTACACGGCCAACCTGGCAGCCTTCCTGACCGTGCAGCGCA
2041   ---------+---------+---------+---------+---------+---------+ 2100
         GCGACTAGTAGTAGAGTAGGATGTGCCGGTTGGACCGTCGGAAGGACTGGCACGTCGCGT
     610 L  I  I  I  S  S  Y  T  A  N  L  A  A  F  L  T  V  Q  R  M 629
```

FIG. 1(E)

```
        TGGATGTGCCCATTGAGTCAGTGGATGACCTGGCTGACCAGACCGCCATTGAATATGGCA
2101    ---------+---------+---------+---------+---------+---------+ 2160
        ACCTACACGGGTAACTCAGTCACCTACTGGACCGACTGGTCTGGCGGTAACTTATACCGT
    630 D   V   P   I   E   S   V   D   D   L   A   D   Q   T   A   I   E   Y   G   T 649

CAATTCACGGAGGCTCCAGCATGACCTTCTTCCAAAATTCCCGCTACCAGACCTACCAAC
2161    ---------+---------+---------+---------+---------+---------+ 2220
        GTTAAGTGCCTCCGAGGTCGTACTGGAAGAAGGTTTTAAGGGCGATGGTCTGGATGGTTG
    650 I   H   G   G   S   S   M   T   F   F   Q   N   S   R   Y   Q   T   Y   Q   R 669

GCATGTGGAATTACATGTATTCCAAGCAGCCCAGCGTGTTCGTGAAGAGCACAGAGGAGG
2221    ---------+---------+---------+---------+---------+---------+ 2280
        CGTACACCTTAATGTACATAAGGTTCGTCGGGTCGCACAAGCACTTCTCGTGTCTCCTCC
    670 M   W   N   Y   M   Y   S   K   Q   P   S   V   F   V   K   S   T   E   E   G 689
                                    EcoRI
                                      |
        GAATCGCCAGGGTGTTGAATTCCAACTACGCCTTCCTCCTGGAATCCACCATGAACGAGT
2281    ---------+---------+---------+---------+---------+---------+ 2340
        CTTAGCGGTCCCACAACTTAAGGTTGATGCGGAAGGAGGACCTTAGGTGGTACTTGCTCA
    690 I   A   R   V   L   N   S   N   Y   A   F   L   L   E   S   T   M   N   E   Y 709

ACTATCGGCAGCGAAACTGCAACCTCACTCAGATTGGGGGCCTGCTGGACACCAAGGGCT
2341    ---------+---------+---------+---------+---------+---------+ 2400
        TGATAGCCGTCGCTTTGACGTTGGAGTGAGTCTAACCCCCGGACGACCTGTGGTTCCCGA
    710 Y   R   Q   R   N   C   N   L   T   Q   I   G   G   L   L   D   T   K   G   Y 729

ATGGGATTGGCATGCCAGTCGGCTCGGTTTTCCGGGACGAGTTTGATCTGGCCATTCTCC
2401    ---------+---------+---------+---------+---------+---------+ 2460
        TACCCTAACCGTACGGTCAGCCGAGCCAAAAGGCCCTGCTCAAACTAGACCGGTAAGAGG
    730 G   I   G   M   P   V   G   S   V   F   R   D   E   F   D   L   A   I   L   Q 749
              PstI
                |
        AGCTGCAGGAGAACAACCGCCTGGAGATCCTGAAGCGCAAATGGTGGGAAGGAGGGAAGT
2461    ---------+---------+---------+---------+---------+---------+ 2520
        TCGACGTCCTCTTGTTGGCGGACCTCTAGGACTTCGCGTTTACCACCCTTCCTCCCTTCA
    750 L   Q   E   N   N   R   L   E   I   L   K   R   K   W   W   E   G   G   K   C 769
                                                            SspI
                                                              |
        GCCCCAAGGAGGAAGATCACAGAGCTAAAGGCCTGGGAATGGAGAATATTGGTGGAATCT
2521    ---------+---------+---------+---------+---------+---------+ 2580
        CGGGGTTCCTCCTTCTAGTGTCTCGATTTCCGGACCCTTACCTCTTATAACCACCTTAGA
    770 P   K   E   E   D   H   R   A   K   G   L   G   M   E   N   I   G   G   I   F 789

TTGTGGTTCTTATTTGTGGCTTAATCGTGGCCATTTTTATGGCTATGTTGGAGTTTTTAT
2581    ---------+---------+---------+---------+---------+---------+ 2640
        AACACCAAGAATAAACACCGAATTAGCACCGGTAAAAATACCGATACAACCTCAAAAATA
    790 V   V   L   I   C   G   L   I   V   A   I   F   M   A   M   L   E   F   L   W 809
```

FIG. 1(F)

```
        GGACTCTCAGACACTCAGAAGCAACTGAGGTGTCCGTCTGCCAGGAGATGGTGACCGAGC
 2641   ---------+---------+---------+---------+---------+---------+ 2700
        CCTGAGAGTCTGTGAGTCTTCGTTGACTCCACAGGCAGACGGTCCTCTACCACTGGCTCG
    810 T  L  R  H  S  E  A  T  E  V  S  V  C  Q  E  M  V  T  E  L 829
             HphI
              |
        TGCGCAGCATTATCCTGTGTCAGGACAGTATCCACCCCCGCCGGCGGCGCGCCGCAGTCC
 2701   ---------+---------+---------+---------+---------+---------+ 2760
        ACGCGTCGTAATAGGACACAGTCCTGTCATAGGTGGGGCGGCCGCCGCGCGGCGTCAGG
    830 R  S  I  I  L  C  Q  D  S  I  H  P  R  R  R  R  A  A  V  P 849

CGCCGCCCCGGCCCCCCATCCCCGAGGAGCGCCGACCGCGGGGCACGGCGACGCTCAGCA
 2761   ---------+---------+---------+---------+---------+---------+ 2820
        GCGGCGGGGCCGGGGGGTAGGGGCTCCTCGCGGCTGGCGCCCCGTGCCGCTGCGAGTCGT
    850 P  P  R  P  P  I  P  E  E  R  R  P  R  G  T  A  T  L  S  N 869

ACGGGAAGCTGTGCGGGGCAGGGGAGCCCGACCAGCTCGCGCAGAGACTGGCGCAGGAGG
 2821   ---------+---------+---------+---------+---------+---------+ 2880
        TGCCCTTCGACACGCCCCGTCCCCTCGGGCTGGTCGAGCGCGTCTCTGACCGCGTCCTCC
    870 G  K  L  C  G  A  G  E  P  D  Q  L  A  Q  R  L  A  Q  E  A 889

CCGCCCTGGTGGCCCGCGGCTGCACGCACATCCGCGTCTGCCCCGAGTGCCGCCGCTTCC
 2881   ---------+---------+---------+---------+---------+---------+ 2940
        GGCGGGACCACCGGGCGCCGACGTGCGTGTAGGCGCAGACGGGGCTCACGGCGGCGAAGG
    890 A  L  V  A  R  G  C  T  H  I  R  V  C  P  E  C  R  R  F  Q 909

AGGGCCTGCGGGCACGGCCGTCGCCCGCCCGCAGCGAGGAGAGCCTGGAGTGGGAGAAAA
 2941   ---------+---------+---------+---------+---------+---------+ 3000
        TCCCGGACGCCCGTGCCGGCAGCGGGCGGGCGTCGCTCCTCTCGGACCTCACCCTCTTTT
    910 G  L  R  A  R  P  S  P  A  R  S  E  E  S  L  E  W  E  K  T 929

CCACCAACAGCAGCGAGCCCGAGTAGTCCCGGAGGCCACAGGACGCGCAGAGGCCGGGCG
 3001   ---------+---------+---------+---------+---------+---------+ 3060
        GGTGGTTGTCGTCGCTCGGGCTCATCAGGGCCTCCGGTGTCCTGCGCGTCTCCGGCCCGC
    930 T  N  S  S  E  P  E  *  936

GGGCGGGAGGGGAGGGGCGGGGCGGGCGCTGCTGTCAGCCGCCAGCCGGAACTTGTACAG
 3061   ---------+---------+---------+---------+---------+---------+ 3120
        CCCGCCCTCCCCTCCCCGCCCCGCCCGCGACGACAGTCGGCGGTCGGCCTTGAACATGTC
            SalI                         BamHI
              |                            |
        CGTCGACACCTCTCCAGATTTCGGATCCAGTCACTTTTCAAAAAGATCAAGGAGCCTGAC
 3121   ---------+---------+---------+---------+---------+---------+ 3180
        GCAGCTGTGGAGAGGTCTAAAGCCTAGGTCAGTGAAAAGTTTTTCTAGTTCCTCGGACTG

GCCCCAGCCAGAGACCGCGCCCGGTCAGGGAGCAGGGTCCACCCGGAAACGTTGCACCCA
 3181   ---------+---------+---------+---------+---------+---------+ 3240
        CGGGGTCGGTCTCTGGCGCGGGCCAGTCCCTCGTCCCAGGTGGGCCTTTGCAACGTGGGT
```

FIG. 1(G)

```
         AAGGGCAAAGGACGGCCCTCCCTCCTGGGCACAAGGACCCATCTTCTCCCAGTGGGTCTT
3241  ----------+---------+---------+---------+---------+---------+ 3300
         TTCCCGTTTCCTGCCGGGAGGGAGGACCCGTGTTCCTGGGTAGAAGAGGGTCACCCAGAA

TCCCTCTCGCCAAAATAACAAGAGTATAGGGTGGGGGGTCCCTACCCAGACCAGTCCAAT
3301  ----------+---------+---------+---------+---------+---------+ 3360
         AGGGAGAGCGGTTTTATTGTTCTCATATCCCACCCCCCAGGGATGGGTCTGGTCAGGTTA

GAATTGGTGGAATCATCAGTTGAATTTCCCCCTAGTCAGGGGCCAATGTACCCTCCGTCT
3361  ----------+---------+---------+---------+---------+---------+ 3420
         CTTAACCACCTTAGTAGTCAACTTAAAGGGGGATCAGTCCCCGGTTACATGGGAGGCAGA
                                                        XmnI
                                                          |
         AGTTCTTACAGAAAAAAAAAAAAAATTAAACAGGGAAGTTTTTCTTTTCTGGATTTGTATA
3421  ----------+---------+---------+---------+---------+---------+ 3480
         TCAAGAATGTCTTTTTTTTTTTTTAATTTGTCCCTTCAAAAAGAAAAGACCTAAACATAT

TTTTTGTTAATGTTCTTTTCCCTTTTCTTTCCTCCTCTCCTTTTCTTCTTTGTCATCTTC
3481  ----------+---------+---------+---------+---------+---------+ 3540
         AAAAACAATTACAAGAAAAGGGAAAAGAAAGGAGGAGAGGAAAAGAAGAAACAGTAGAAG

TCAGTCCTGTTAATTTGTTTTGTGTTTTTTGGAGGGGAGGCTGGGTTAGGGAATGGAAG
3541  ----------+---------+---------+---------+---------+---------+ 3600
         AGTCAGGACAATTAAACAAAACACAAAAAACCTCCCCCTCCGACCCAATCCCTTACCTTC
                                                       SspI
                                                         |
         CCTAAATAATCCCTATTTCTTCTTTTTCCTGAATTTTGGAATATTGCGTTACCAGTGCAT
3601  ----------+---------+---------+---------+---------+---------+ 3660
         GGATTTATTAGGGATAAAGAAGAAAAAGGACTTAAAACCTTATAACGCAATGGTCACGTA
                                                   HphI  PstI
                                                    |     |
         CCGATTTCAGGTGCGGAACTCTCTGTATGGTGACTGAGGGGCCTGCAG
3661  ----------+---------+---------+---------+-------- 3708
         GGCTAAAGTCCACGCCTTGAGAGACATACCACTGACTCCCCGGACGTC
```

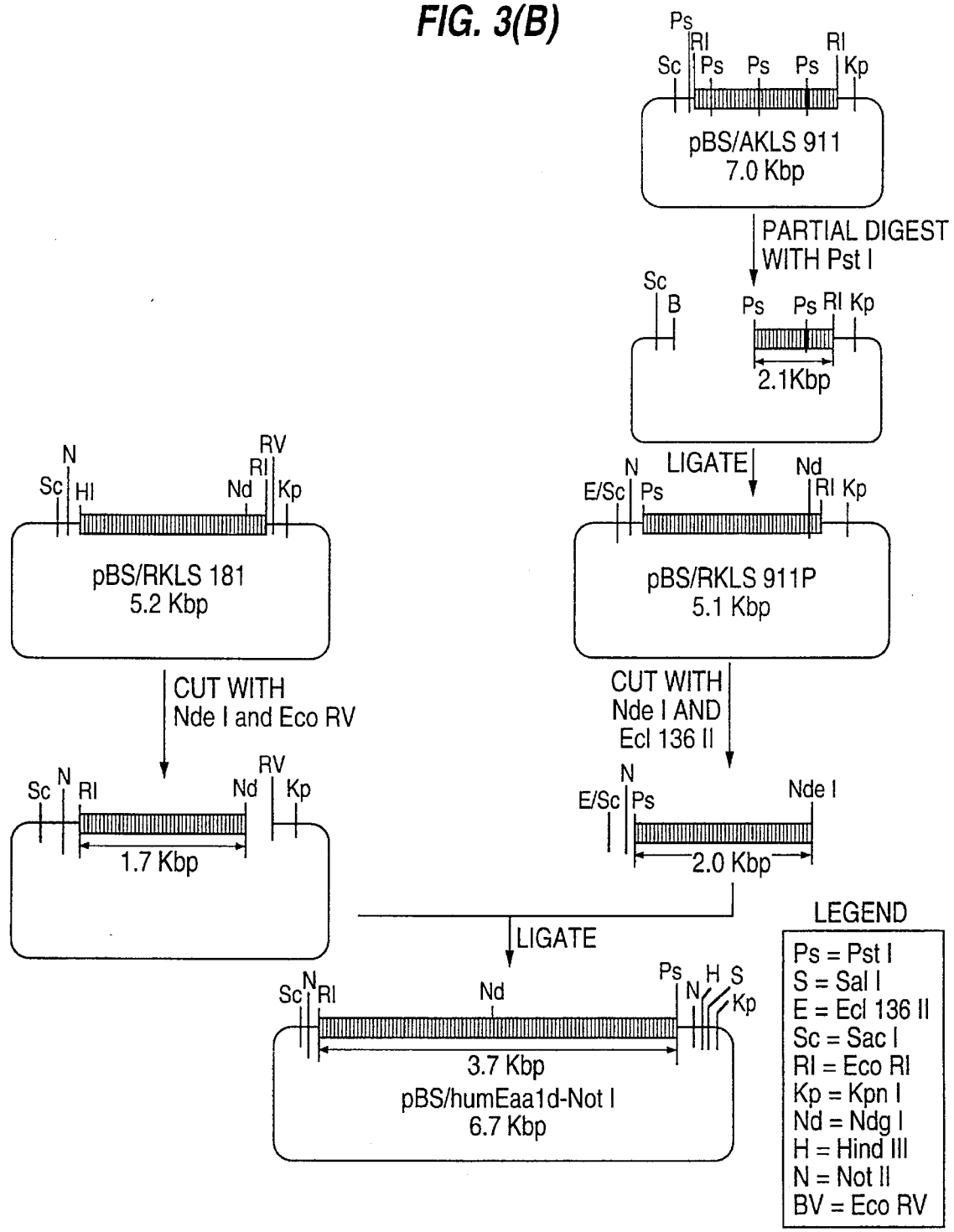

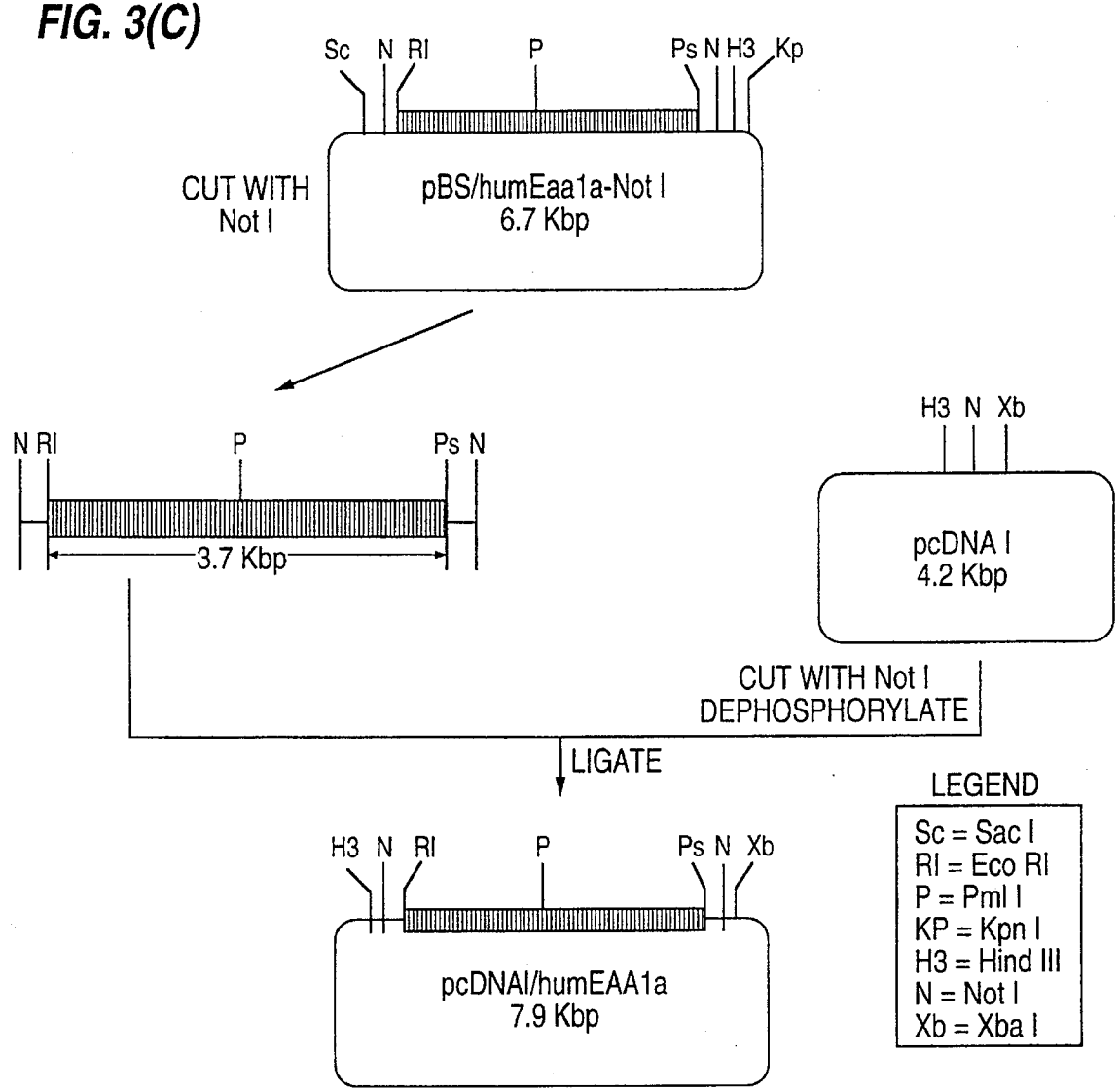

FIG. 4(B)

```
                                                                                    1748
                                                                                     v
                              GTTTTGCTGCA                                           GTT
HUMAN EAA 1d       CGTCACCACCATCCT <> GGAAAACCCATATATTTAATGCTGAAGGGGAACCAC ------//------ Val 1737
                                                                                     v
HUMAN EAA 1a       CGTCACCACCATCCT <> GGAAAAACCCATATATTTAATGCTGAAGGGGAACCAC ------//------ GTT
       NUCLEOTIDE   ^                                                                Val
              1412
                                                                                    1737
                                                                                     v
HUMAN EAA 1b       CGTCACCACCATCCT <> GGAAAAACCCATATATTTAATGCTGAAGGGGAACCAC ------//------ ATT
                                                                                     Ile 1713
                                                                                     v
HUMAN EAA 1c       CGTCACCACCATCCT <> ..................GGGGAACCAC ------//------ ATT
                                                                                     Ile
```

KAINATE-BINDING HUMAN CNS RECEPTORS OF THE EAA1 FAMILY

This application is a continuation of application Ser. No. 08/091,441, filed Jul. 15, 1993, now abandoned, which is a divisional application of Ser. No. 07/750,090, filed Aug. 26, 1991 now abandoned.

FIELD OF THE INVENTION

This invention is concerned with applications of recombinant DNA technology in the field of neurobiology. More particularly, the invention relates to the cloning and expression of DNA coding for excitatory amino acid (EAA) receptors, especially human EAA receptors.

BACKGROUND TO THE INVENTION

In the mammalian central nervous system (CNS), the transmission of nerve impluses is controlled by the interaction between a neurotransmitter substance released by the "sending" neuron and a surface receptor on the "receiving" neuron. L-glutamate is the most abundant neurotransmitter in the CNS, and mediates the major excitatory pathway in vertebrates. Glutamate is therefore referred to as an excitatory amino acid (EAA) and the receptors which respond to it are variously referred to as glutamate receptors, or more commonly as EAA receptors.

Using tissues isolated from mammalian brain, and various synthetic EAA receptor agonists, knowledge of EAA receptor pharmacology has been refined somewhat. Members of the EAA receptor family are now grouped into three main types based on differential binding to such agonists. One type of EAA receptor, which in addition to glutgate also binds the agonist NMDA (N-methyl-D-aspartate), is referred to as the NMDA type of EAA receptor. Two other glutamate-binding types of EAA receptor, which do not bind NMDA, are named according to their preference for binding with two other EAA receptor agonists, namely AMPA (alpha-amino-3-hydroxy-5-methyl-isoxazole-4-propionate), and kainate. Particularly, receptors which bind glutamate but not NMDA, and which bind with greater affinity to kainate than to AMPA, are referred to as kainate type EAA receptors. Similarly, those EAA receptors which bind glutamate but not NMDA, and which bind AMPA with greater affinity than kainate are referred to as AMPA type EAA receptors.

This family of glutamate-binding EAA receptors is of great physiological and medical importance. Glutamate is involved in many aspects of long-term potentiation (learning and memory), in the development of synaptic plasticity, in epileptic seizures, in neuronal damage caused by ischemia following stroke or other hypoxic events, as well as in other forms of neurodegenerative processes. However, the development of therapeutics which modulate these processes has been very difficult, due to the lack of any homogeneous source of receptor material with which to discover selectively binding drug molecules, which interact specifically at the interface of the EAA receptor. The brain derived tissues currently used to screen candidate drugs are heterogeneous receptor sources, possessing on their surface many receptor types which interfere with studies of the EAA receptor/ligand interface of interest. The search for human therapeutics is further complicated by the limited availability of brain tissue of human origin. It would therefore be desirable to obtain cells that are genetically engineered to produce only the receptor of interest. With cell lines expressing cloned receptor genes, a substrate which is homogeneous for the desired receptor is provided, for drug screening programs.

Very recently, genes encoding substituent polypeptides of EAA receptors from non-human sources, principally rat, have been discovered. Hollmann et al., Nature 342: 643, 1989 described the isolation from rat of a gene referred to originally as GluR-K1 (but now called simply GluR1). This gene encodes a member of the rat EAA receptor family, and was originally suspected as being of the kainate type. Subsequent studies by Keinanen et al., Science 249: 556, 1990, showed, again in rat, that a gene called GluR-A, which was in fact identical to the previously isolated GluR1, in fact encodes a receptor not of the kainate type, but rather of the AMPA type. These two groups of researchers have since reported as many as five related genes isolated from rat sources. Boulter et al., Science 249: 1033, 1990, revealed that, in addition to GluR1, the rat contained 3 other related genes, which they called GluR2, GluR3, and GluR4, and Bettler et al., Neuron 5: 583. 1990 described GluR5. Keinanen et al., supra, described genes called GluR-A, GluR-B, GluR-C and GluR-D which correspond precisely to GluR1, GluR2, GluR3 and GluR4 respectively. Sommer et al., Science 249: 1580, 1990 also showed, for GluR-A, GluR-B, GluR-C and GluR-D two alternatively spliced forms for each gene. These authors, as well as Monyer et al., Neuron 6: 799, 1991 were able to show that the differently spliced versions of these genes were differentially expressed in the rat brain. In addition to the isolation of these AMPA receptor genes, several studies have more recently attempted to determine the ion-gating properties of different mixtures of the known receptors (Nakanishi et al., Neuron 5: 569, 1990; Hollmann et al., Science 252: 851, 1991; Verdoorn et al., Science 252: 1715, 1991; and see WO 91/06648).

Some recent work has also been published regarding non-human genes which appear to encode the kainate-type of receptor. Egebjerg et at., Nature 351: 745, 1991, have described the isolation of a gene from rat called GluR6, which although related in sequence to the AMPA receptor genes, forms a receptor which is not activated by AMPA but rather by glutamate, quisqualate, and preferentially, kainate. Other kainate-binding proteins have been described from frog (Wada et at., Nature 342: 684, 1989), chicken (Gregor et at., Nature 342: 689, 1989) and from rat (Werner et at., Nature 351: 742, 1991). These latter genes encode proteins which bind kainate, but which do not readily form into functional ion channels when expressed by themselves.

There has emerged from these molecular cloning advances a better understanding of the structural features of EAA receptors and their subunits, as they exist in the rat brain. According to the current model of EAA receptor structure, each is heteromeric in structure, consisting of individual membrane-anchored subunits, each having four transmembrane regions, and extracellular domains that dictate ligand binding properties to some extent and contribute to the ion-gating function served by the receptor complex. Keinanen et al, supra, have shown for example that each subunit of the rat GluR receptor, including those designated GluR-A, GluR-B, GluR-C and GluR-D, display cation channel activity gated by glutamate, by AMPA and by kainate, in their unitary state. When expressed in combination however, for example GluR-A in combination with GluR-B, gated ion channels with notably larger currents are produced by the host mammalian cells.

In the search for therapeutics useful to treat CNS disorders in humans, it is highly desirable of course to provide a screen for candidate compounds that is more representative of the human situation than is possible with the rat receptors isolated to date. It is particularly desirable to provide cloned genes coding for human receptors, and cell lines expressing those genes, in order to generate a proper screen for human therapeutic compounds. These, accordingly, are objects of the present invention.

It is another object of the present invention to provide in isolated form a DNA molecule which codes for a human EAA receptor.

It is another object of the present invention to provide a cell that has been genetically engineered to produce a kainate-binding human EAA receptor.

Other objects of the present invention will be apparent from the following description of the invention.

SUMMARY OF THE INVENTION

Genes coding for a family of EAA receptors endogenous to human brain have now been identified and characterized. A representative member of this human EAA receptor family, designated human EAA1a, codes for a receptor protein that in addition to binding glutamate with an affinity typical of EAA receptors, also exhibits ligand binding properties characteristic of kainate-type EAA receptors. Sequence-related genes coding for naturally occurring variants of the human EAA1a receptor have also been identified, and constitute additional members of this receptor family, herein referred to as the human EAA1 receptor family.

The present invention thus provides, in one of its aspects, an isolated polynucleotide, consisting either of DNA or of RNA, which codes for a human EAA1 receptor or for a kainate-binding fragment thereof.

In another aspect of the present invention, there is provided a cell that has been genetically engineered to produce a kainate-binding, human EAA receptor belonging to the herein-defined EAA1 family. In related aspects of the present invention, there are provided recombinant DNA constructs and relevant methods useful to create such cells.

In another aspect of the present invention, there is provided a method for evaluating the the affinity of a selected compound for binding to a receptor having the characteristics of a human EAA1 receptor, which comprises the steps of incubating the compound with a genetically engineered cell of the present invention, or with a membrane preparation derived therefrom, in a manner suitable to determine the receptor binding affinity of the test compound.

Other aspects of the present invention, which encompass various applications of the discoveries herein described, will become apparent from the following detailed description, and from the accompanying drawings, in which:

BRIEF REFERENCE TO THE DRAWINGS

FIGS. 1(A) to to 1(G) provide the nucleotide sequence (SEQ ID NO: 1) of DNA coding for an excitatory amino acid receptor of the present invention, and the deduced amino acid sequence (SEQ ID NO: 2) thereof, FIG. 2 illustrates schematically a PCR-based strategy for amplifying the DNA sequence illustrated in FIG. 1 (primers 1–8 are shown in SEQ ID NOS. 3–10, respectively), FIGS. 3(A), 3(B) and 3(C) illustrate with linear plasmid maps the strategy used to construct expression vectors harbouring the DNA sequence illustrated in FIG. 1 (the sequences shown in FIG. 3(1) are also disclosed in SEQ ID NOS. 11 and 12);

FIGS. 4(A) and 4(B) (SEQ ID NOS. 13–15) show, with reference to FIG. 1, the DNA and amino acid sequences of naturally occurring variants of the EAA receptor illustrated in FIG. 1; and FIG. 5 illustrates graphically the ligand-binding properties of the EAA receptor expressed from the coding region provided in FIG. 1.

DETAILED DESCRIPTION OF THE INVENTION AND ITS PREFERRED EMBODIMENTS

The invention relates to excitatory amino acid (EAA) receptors of human origin, and is directed more particularly to a novel family of kainate-type human EAA receptors, herein designated the human EAA1 receptor family. As used herein, the term "human EAA1 receptor" is intended to embrace the human EAA1a receptor, and kainate-binding variants of the EAA1a receptor that are structurally related thereto, i.e. have at least 95% homology therewith, including naturally occurring and synthetically derived variants of the EAA1a receptor. Naturally occurring variants of the human EAA1a receptor include particularly the receptors herein designated human EAA1b receptor, human EAA1c receptor and human EAA1d receptor. As used herein, the term "kalnate-binding" refers to receptor variants and receptor fragments that display greater binding affinity for kainate than for either glutamate, AMPA or NMDA, as determined in assays of conventional design, such as the assays herein described.

Each of the naturally occurring members of the EAA1 family possesses structural features characteristic of the EAA receptors in general, including extracellular N- and C-terminal regions, as well as four internal hydrophobic domains which serve to anchor the receptor within the cell surface membrane. The particular human EAA receptor designated EAA1a is a protein characterized structurally as a single polypeptide chain that is produced initially in precursor form bearing an 20 residue N-terminal signal peptide, and is transported to the cell surface in mature form, lacking the signal peptide and consisting of 936 amino acids arranged in the sequence illustrated, by single letter code, in FIG. 1 (SEQ ID NOS. 1 and 2). Unless otherwise stated, amino acid residues of the EAA1 receptors are numbered with reference to the mature protein sequence. With respect to structural domains of the receptor, hydropathy analysis reveals four putative transmembrane domains, one spanning residues 527–546 inclusive (TM-1), another spanning residues 571–589 (TM-2), a third spanning residues 600–618 (TM-3) and the fourth spanning residues 785–805 (TM-4). Based on this assignment, it is likely that the human EAA1a receptor structure, in its natural membrane-bound form, consists of a 526 amino acid N-terminal extracellular domain, followed by a hydrophobic region containing four transmembrane domains and an extracellular, 131 amino acid C-terminal domain.

Figure 4A:
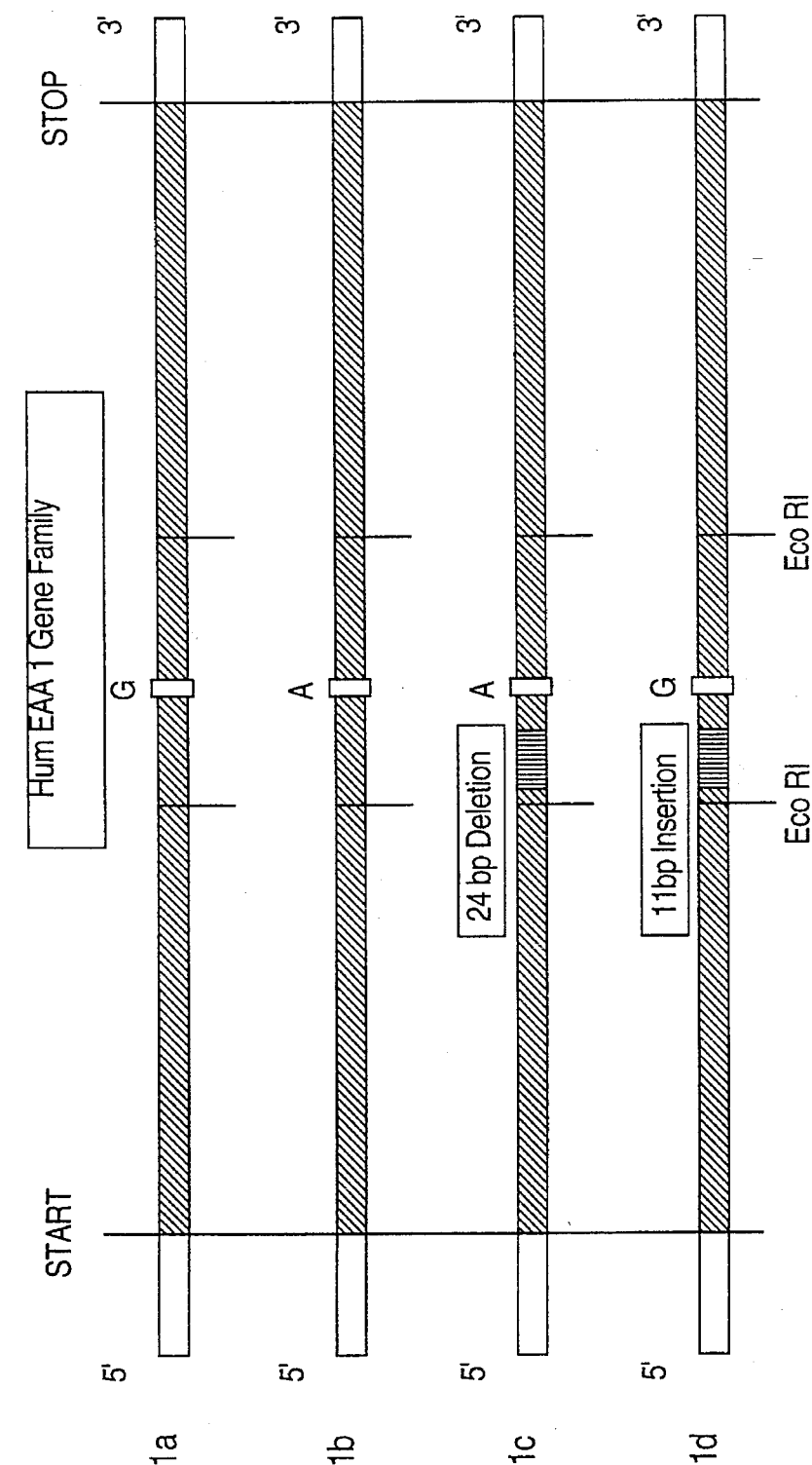

As shown in FIG. 4, structurally related variants of the EAA1a (shown partially in SEQ ID NO: 14) receptor, which occur naturally in human brain tissue, have also been identified. As deduced from nucleotide sequences of the genes coding for them, these variants share at least about 98% amino acid homology with EAA1a, i.e., have at least about 98% identity at the amino acid level, with respect to EAA1a. One variant, designated EAA1 b, is virtually identical to EAA1a (shown partially in SEQ ID NO: 14) except for a single nucleotide difference, which results in a GTT to ATT codon substitution, and a valine to isoleucine change at the amino acid level. The two other variants, designated EAA1c (shown partially in SEQ ID NO: 15) and EAA1d (shown partially in SEQ ID NO: 13) incorporate more substantial variations relative to EAA1a. The variant EAA1c is characterized by a 24 base pair deletion which results, at the amino acid level, in an eight residue deletion from an extracellular domain of the EAA1a receptor. The variant EAA1d, on the other hand, is characterized by an 11 nucleotide insertion at precisely the location where the 24 nucleotide deletion occurs in EAA1c. The 11 base pair insertion contained in EAA1d has the effect of shifting the reading frame, and in fact introduces stop codons at a location 3' of and neighbouring the insertion. As a result, the EAA1d-encoding DNA in fact encodes a truncated protein or, in essence, an extracellular fragment of EAA1a.

In human hippocampal cDNA libraries, the source from which DNA coding for the EAA1a receptor was isolated, the EAA1a receptor is encoded by the nucleotide sequence provided in FIG. 1 (SEQ ID NOS. 1 and 2). Relative to EAA receptors previously discovered in rat tissue, as described in the publications mentioned hereinabove, members of the human EAA1 receptor family share not more than about 45% amino acid identity with such rat receptors, with the exception of the rat KA-1 protein described very recently by Werner et al, 1991, supra, which shares about 94% amino acid homology (identity) with human EAA1a. The human EAA1 receptors differ most significantly from this rat receptor in the extracellular, C-terminal region of the receptors.

Like other members of the human EAA1 receptor family, receptor subtype EAA1a is characterized by a pharmacological profile i.e. a ligand binding "signature", that points strongly to a kainate-type pharmacology, as distinct from other excitatory amino acid receptor types, such as NMDA and AMPA. Despite the understanding that kainate binding receptors require a multi- and perhaps heteromeric subunit structure to function in the pharmacological sense, it has been found that cells producing the unitary EAA1a receptor do, independently of association with other receptor subunits, provide a reliable indication of excitatory amino acid binding. Thus, in a key aspect of the present invention, the human EAA1a receptor is exploited for the purpose of screening candidate compounds for the ability to compete with endogenous EAA receptor ligands and known synthetic analogues thereof, for EAA receptor binding.

For use in receptor binding assays, it is desirable to construct by application of genetic engineering techniques a mammalian cell that produces a human EAA1 receptor in functional form as a heterologous product. The construction of such cell lines is achieved by introducing into a selected host cell a recombinant DNA construct in which DNA coding for the human EAA1 receptor in a form transportable to the cell surface i.e., bearing its native signal peptide or a functional, heterologous equivalent thereof, is associated with expression controlling elements that are functional in the selected host to drive expression of the receptor-encoding DNA, and thus elaborate the desired EAA 1 receptor protein. Such cells are herein characterized as having the receptor-encoding DNA incorporated "expressibly" therein. The receptor-encoding DNA is referred to as "heterologous" with respect to the particular cellular host if such DNA is not naturally found in the particular host. The particular cell type selected to serve as host for production of the human EAA1 receptor can be any of several cell types currently available in the art, but should not of course be a cell type that in its natural state elaborates a surface receptor that can bind excitatory amino acids, and so confuse the assay results sought from the engineered cell line. Generally, such problems are avoided by selecting as host a non-neuronal cell type, and can further be avoided using non-human cell lines, as is conventional. It will be appreciated that neuronal- and human-type cells may nevetheless serve as expression hosts, provided that "background" binding to the test ligand is accounted for in the assay results.

According to one embodiment of the present invention, the cell line selected to serve as host for EAA1 receptor production is a mammalian cell. Several types of such cell lines are currently available for genetic engineering work, and these include the chinese hamster ovary (CHO) cells for example of K1 lineage (ATCC CCL 61) including the Pro5 variant (ATCC CRL 1281); the fibroblast-like cells derived from SV40-transformed African Green monkey kidney of the CV-1 lineage (ATCC CCL 70), of the COS-1 lineage (ATCC CRL 1650) and of the COS-7 lineage (ATCC CRL 1651); murine L-cells, murine 3T3 cells (ATCC CRL 1658), murine C127 cells, human embryonic kidney cells of the 293 lineage (ATCC CRL 1573), human carcinoma cells including those of the HeLa lineage (ATCC CCL 2), and neuroblastoma cells of the lines IMR-32 (ATCC CCL 127), SK-N-MC (ATCC HTB 10) and SK-N-SH (ATCC HTB 11).

A variety of gene expression systems have been adapted for use with these hosts and are now commercially available, and any one of these systems can be selected to drive expression of the EAA1 receptor-encoding DNA. These systems, available typically in the form of plasmidic vectors, incorporate expression cassettes the functional components of which include DNA constituting expression controlling sequences, which are host-recognized and enable expression of the receptor-encoding DNA when linked 5' thereof. The systems further incorporate DNA sequences which terminate expression when linked 3' of the receptor-encoding region. Thus, for expression in the selected mammalian cell host, there is generated a recombinant DNA expression construct in which DNA coding for the transportable receptor precursor is linked with expression controlling DNA sequences recognized by the host, and which include a region 5' of the receptor-encoding DNA to drive expression, and a 3' region to terminate expression. The plasmidic vector harbouring the expression construct typically incorporates such other functional components as an origin of replication, usually virally-derived, to permit replication of the plasmid in the expression host and desirably also for plasmid amplification in a bacterial host, such as *E. coli*. To provide a marker enabling selection of stably transformed recombinant cells, the vector will also incorporate a gene conferring some survival advantage on the transformants, such as a gene coding for neomycin resistance in which case the transformants are plated in medium supplemented with neomycin.

Included among the various recombinant DNA expression systems that can be used to achieve mammalian cell expression of the receptor-encoding DNA are those that exploit promoters of viruses that infect mammalian cells, such as the promoter from the cytomegalovirus (CMV), the Rous sarcoma virus (RSV), simian virus (SV40), murine mammary tumor virus (MMTV) and others. Also useful to drive expression are promoters such as the LTR of retroviruses, insect cell promoters such as those regulated by temperature, and isolated from Drosophila, as well as mammalian gene promoters such as those regulated by heavy metals i.e. the metalothionein gene promoter, and other steroid-inducible promoters.

For incorporation into the recombinant DNA expression vector, DNA coding for the desired EAA1 receptor, i.e. the EAA1a receptor or a kalnate-binding variant thereof, can be obtained by applying selected techniques of gene isolation or gene synthesis. As described in more detail in the examples herein, the EAA1a receptor, and the EAA1b, EAA1c and EAA1d variants thereof, are encoded within the genome of human brain tissue, and can therefore be obtained by careful application of conventional gene isolation and cloning techniques. This typically will entail extraction of total messenger RNA from a fresh source of human brain tissue, preferably cerebellum or hippocampus tissue, followed by conversion of message to cDNA and formation of a library in for example a bacterial plasmid, more typically a bacteriophage. Such bacteriophage harbouring fragments of the human DNA are typically grown by plating on a lawn of susceptible E. coli bacteria, such that individual phage plaques or colonies can be isolated. The DNA carried by the phage colony is then typically immobilized on a nitrocellulose or nylon-based hybridization membrane, and then hybridized, under carefully controlled conditions, to a radioactively (or otherwise) labelled oligonucleotide probe of appropriate sequence to identify the particular phage colony carrying receptor-encoding DNA or fragment thereof. Typically, the gene or a portion thereof so identified is subcloned into a plasmidic vector for nucleic acid sequence analysis.

Having herein provided the nucleotide sequence of various human EAA1 receptors, it will be appreciated that automated techniques of gene synthesis and/or amplification can be performed to generate DNA coding therefor. Because of the length of the EAA1 receptor-encoding DNA, application of automated synthesis may require staged gene construction, in which regions of the gene up to about 300 nucleotides in length are synthesized individually and then ligated in correct succession for final assembly. Individually synthesized gene regions can be amplified prior to assembly, using polymerase chain reaction (PCR) technology.

The application of automated gene synthesis techniques provides an opportunity for generating sequence variants of naturally occurring members of the EAA1 gene family. It will be appreciated, for example, that polynucleotides coding for the EAA1 receptors herein described can be generated by substituting synonymous codons for those represented in the naturally occurring polynucleotide sequences herein identified. In addition, polynucleotides coding for synthetic variants of the EAA1 receptors herein described can be generated which for example incorporate one or more single amino acid substitutions, deletions or additions. Since it will for the most part be desirable to retain the natural ligand binding profile of the receptor for screening purposes, it is desirable to limit amino acid substitutions, for example to the so-called conservative replacements in which amino acids of like charge are substituted, and to limit substitutions to those sites less critical for receptor activity e.g. within about the first 20 N-terminal residues of the mature receptor, and such other regions as are elucidated upon receptor domain mapping.

With appropriate template DNA in hand, the technique of PCR amplification may also be used to directly generate all or part of the final gene. In this case, primers are synthesized which will prime the PCR amplification of the final product, either in one piece, or in several pieces that may be ligated together. This may be via step-wise ligation of blunt ended, amplified DNA fragments, or preferentially via step-wise ligation of fragments containing naturally occurring restriction endonuclease sites. In this application, it is possible to use either cDNA or genomic DNA as the template for the PCR amplification. In the former case, the cDNA template can be obtained from commercially available or self-constructed cDNA libraries of various human brain tissues, including hippocampus and cerebellum.

Once obtained, the receptor-encoding DNA is incorporated for expression into any suitable expression vector, and host cells are transfected therewith using conventional procedures, such as DNA-mediated transformation, electroporation, or particle gun transformation. Expression vectors may be selected to provide transformed cell lines that express the receptor-encoding DNA either transiently or in a stable manner. For transient expression, host cells are typically transformed with an expression vector harbouring an origin of replication functional in a mammalian cell. For stable expression, such replication origins are unnecessary, but the vectors will typically harbour a gene coding for a product that confers on the transformants a survival advantage, to enable their selection. Genes coding for such selectable markers include the E. coli gpt gene which confers resistance to mycophenolic acid, the neo gene from transposon Tn5 which confers resistance to the antibiotic G418 and to neomycin, the dhfr sequence from murine cells or E. coli which changes the phenotype of DHFR– cells into DHFR+ cells, and the tk gene of herpes simplex virus, which makes TK– cells phenotypically TK+ cells. Both transient expression and stable expression can provide transformed cell lines, and membrane preparations derived therefrom, for use in ligand screening assays.

For use in screening assays, cells transiently expressing the receptor-encoding DNA can be stored frozen for later use, but because the rapid rate of plasmid replication will lead ultimately to cell death, usually in a few days, the transformed cells should be used as soon as possible. Such assays may be performed either with intact cells, or with membrane preparations derived from such cells. The membrane preparations typically provide a more convenient substrate for the ligand binding experiments, and are therefore preferred as binding substrates. To prepare membrane preparations for screening purposes, i.e., ligand binding experiments, frozen intact cells are homogenized while in cold water suspension and a membrane pellet is collected after centrifugation. The pellet is then washed in cold water, and dialyzed to remove endogenous EAA ligands such as glutamate, that would otherwise compete for binding in the assays. The dialyzed membranes may then be used as such, or after storage in lyophilized form, in the ligand binding assays. Alternatively, intact, fresh cells harvested about two days after transient transfection or after about the same period following fresh plating of stably transfected cells, can be used for ligand binding assays by the same methods as used for membrane preparations. When cells are used, the cells must be harvested by more gentle centrifugation so as not to damage them, and all washing must be done in a buffered medium, for example in phosphate-buffered saline, to avoid osmotic shock and rupture of the cells.

The binding of a candidate ligand to a selected human EAA1 receptor of the invention is evaluated typically using a predetermined amount of cell-derived membrane (measured for example by protein determination), generally from about 25 ug to 100 ug. Generally, competitive binding assays will be useful to evaluate the affinity of a test compound relative to kainate. This competitive binding assay can be performed by incubating the membrane preparation with radiolabelled kainate, for example [3H]-kainate, in the presence of unlabelled test compound added at varying concentrations. Following incubation, either displaced or bound radiolabelled kainate can be recovered and measured, to determine the relative binding affinities of the test compound and kainate for the particular receptor used as substrate. In this way, the affinities of various compounds for the kainate-type human EAA receptors can be measured.

As an alternative to using cells that express receptor-encoding DNA, ligand characterization may also be performed using cells for example Xenopus oocytes, that yield functional membrane-bound receptor following introduction of messenger RNA coding for the EAA1 receptor. In this case, the EAA1 receptor gene of the invention is typically subcloned into a plasmidic vector such that the introduced gene may be easily transcribed into RNA via an adjacent RNA transcription promoter supplied by the plasmidic vector, for example the T3 or T7 bacteriophage promoters. RNA is then transcribed from the inserted gene in vitro, and can then be injected into Xenopus oocytes. Following the injection of nL volumes of an RNA solution, the oocytes are left to incubate for up to several days, and are then tested for the ability to respond to a particular ligand molecule supplied in a bathing solution. Since functional EAA receptors act in part by operating a membrane channel through which ions may selectively pass, the functioning of the receptor in response to a particular ligand molecule in the bathing solution may typically be measured as an electrical current utilizing microelectrodes inserted into the cell.

In addition to using the receptor-encoding DNA to construct cell lines useful for ligand screening, expression of the DNA can, according to another aspect of the invention, be performed to produce fragments of the receptor in soluble form, for structure investigation, to raise antibodies and for other experimental uses. It is expected that the portion of the EAA1 receptor responsible for binding a ligand molecule resides on the outside of the cell, i.e., is extracellular. It is therefore desirable in the first instance to facilitate the characterization of the receptor-ligand interaction by providing this extracellular ligand-binding domain in quantity and in isolated form, i.e., free from the remainder of the receptor. To accomplish this, the full-length EAA1 receptor-encoding DNA may be modified by site-directed mutagenesis, so as to introduce a translational stop codon into the extracellular N-terminal region, immediately before the sequence encoding the first transmembrane domain (TM1), i.e., before residue 527 as shown in FIG. 1 (SEQ ID NOS: 1 and 2). Since there will no longer be produced any transmembrane domain(s) to "anchor" the receptor into the membrane, expression of the modified gene will result in the secretion, in soluble form, of only the extracellular ligand-binding domain. Standard ligand-binding assays may then be performed to ascertain the degree of binding of a candidate compound to the extracellular domain so produced. It may of course be necessary, using site-directed mutagenesis, to produce several different versions of the extracellular regions, in order to optimize the degree of ligand binding to the isolated domains.

Alternatively, it may be desirable to produce an extracellular domain of the receptor which is not derived from the amino-terminus of the mature protein, but rather from the carboxy-terminus instead, for example domains immediately following the fourth transmembrane domain (TM4), i.e., residing between amino acid residues 805 and 936 inclusive of FIG. 1 (SEQ ID NOS. 1 and 2). In this case, site-directed mutagenesis and/or PCR-based amplification techniques may readily be used to provide a defined fragment of the gene encoding the receptor domain of interest. Such a DNA sequence may be used to direct the expression of the desired receptor fragment, either intracellularly, or in secreted fashion, provided that the DNA encoding the gene fragment is inserted adjacent to a translation start codon provided by the expression vector, and that the required translation reading frame is carefully conserved.

It will be appreciated that the production of such extracellular ligand binding domains may be accomplished in a variety of host cells. Mammalian cells such as CHO cells may be used for this purpose, the expression typically being driven by an expression promoter capable of high-level expression, for example the CMV (cytomegalovirus) promoter. Alternately, non-mammalian cells, such as insect Sf9 (Spodoptera frugiperda) cells may be used, with the expression typically being driven by expression promoters of the baculovirus, for example the strong, late polyhedrin protein promoter. Filamentous fungal expression systems may also be used to secrete large quantities of such extracellular domains of the EAA receptor. Aspergillus nidulans, for example, with the expression being driven by the alcA promoter, would constitute such an acceptable system. In addition to such expression hosts, it will be further appreciated that any prokaryotic or other eukaryotic expression system capable of expressing heterologous genes or gene fragments, whether intracellularly or extracellularly would be similarly acceptable.

The availability of isolated extracellular ligand-binding domains of the receptor protein makes it feasible to determine the 3-dimensional structures of these ligand-binding regions, with or without a candidate ligand complexed thereto, by a combination of X-ray crystallographic and advanced 2D-NMR techniques. In this way, additional new candidate compounds, predicted to have the required interactions with the 3-dimensional receptor structure, can be specifically designed and tested.

With large domains, crystallography is the method of choice for structure determination of both the domain in isolation, and of the co-complex with the natural ligand (or an appropriate antagonist or agonist molecule). If a particular domain can be made small enough, for example approximately 100–130 amino acids in length, then the powerful technique of 2-D NMR can also be applied to structure determination, This enables not only the determination of the domain structure, but also provides dynamic information about the drug-receptor interaction.

For use particularly in detecting the presence and/or location of an EAA1 receptor, for example in brain tissue, the present invention also provides, in another of its aspects, labelled antibody to a human EAA1 receptor. To raise such antibodies, there may be used as immunogen either the intact, soluble receptor or an immunogenic fragment thereof, produced in a microbial or mammalian cell host as described above or by standard peptide synthesis techniques. Regions of the EAA1a receptor particularly suitable for use as immunogenic fragments include those corresponding in sequence to an extracellular region of the receptor, or a portion of the extracellular region, such as peptides consisting of residues 1–526, including particularly residues 106–120 or 178–191 or 463–509, and peptides corresponding to the region between transmembrane domains TM-2 and TM-3, such as a peptide consisting of residues 590–599. Peptides consisting of the C-terminal domain (residues 806–936), or fragment thereof such as a peptide consisting of residues 895–936 or 915–930, may also be used for the raising of antibodies. Substantially the same regions of the human EAA1b, EAA1c and EAA1d receptors may also be used for production of antibodies against these receptors.

The raising of antibodies to the desired EAA1 receptor or immunogenic fragment can be achieved, for polyclonal antibody production, using immunization protocols of conventional design, and any of a variety of mammalian hosts, such as sheep, goats and rabbits. Alternatively, for monoclonal antibody production, immunocytes such as splenocytes can be recovered from the immunized animal and fused, using hybridoma technology, to a myeloma cells. The fusion products are then screened by culturing in a selection medium, and cells producing antibody are recovered for continuous growth, and antibody recovery. Recovered antibody can then be coupled covalently to a detectable label, such as a radiolabel, enzyme label, luminescent label or the like, using linker technology established for this purpose.

In detectably labelled form, e.g. radiolabelled form, DNA or RNA coding for the human EAA1 receptor, and selected regions thereof, may also be used, in accordance with another aspect of the present invention, as hybridization probes for example to identify sequence-related genes resident in the human or other mammalian genomes (or cDNA libraries) or to locate the EAA1-encoding DNA in a specimen, such as brain tissue. This can be done using either the intact coding region, or a fragment thereof having radiolabelled e.g. $^{32}P$, nucleotides incorporated therein. To identify the EAA1-encoding DNA in a specimen, it is desirable to use either the full length cDNA coding therefor, or a fragment which is unique thereto. With reference to FIG. 1 and the nucleotide numbering appearing thereon, such nucleotide fragments include those corresponding in sequence to a region coding for the N-terminus or C-terminus of the receptor, or representing a 5'-untranslated or 3'-untranslated region thereof, such as one of the following nucleotide regions: 8–156, 157–1563, 531–575, 1278–1359, 2826–2909, 2958–3073 and 3024–3708. These sequences, and the intact gene itself, may also be used of course to clone EAA1-related human genes, particularly cDNA equivalents thereof, by standard hybridization techniques.

EXAMPLE 1

Isolation of DNA Coding For The Human EAA1a Receptor

As a first step in the isolation of DNA coding for a human EAA receptor, the published nucleotide sequences of rat GluR1 receptor, and chicken and frog kainate binding proteins were compared to identify spaced regions of homology, capable of serving as sites for primer binding, and PCR-based amplification. Oligonucleotide primers putatively capable of hybridizing with sequence-related regions in human cDNA, and having non-hybridizing flanks bearing HindIII restriction sites for subsequent cloning work, were then synthesized based on the published sequence of the rat GluR1 gene using conventional techniques of gene synthesis, to generate primers of the following sequence:

(SEQ ID NO:16)
5' GGGGTTTAAGCTTGAGCGTCGTCCTCTTCCTGGT 3'

(SEQ ID NO:17)
5' GGGGTTTAAGCTTGTGAAGAACCACCAGACGCCG 3'

Using human hippocampal cDNA as template (obtained as an EcoRI-based lambda gt10 library from Clontech Laboratories (Palo Alto, Calif., U.S.A.) the primers were then used in an attempt to amplify homologous sequences in the human cDNA, by application of the polymerase chain reaction technique. Reaction mixtures contained, in 100 ul, 100 ng of human hippocampal cDNA, 125 pmol of each primer and 2U Taq polymerase (in 10 mM Tris-HCl, pH9.0, 50 mM KCl, 1.5 mM $MgCl_2$, and with 0.2 mM of each deoxyribonucleotide species). There were then performed thirty cycles of 94C/1 min; 58C/1 min; 72C/2 min, followed by a final cycle of 72C/30 min.

There was generated an amplification product having an expected nucleotide length (239 bp). The product of amplification was then liberated from the gel and sub-cloned for sequencing into the HindIII site of phagemid vector pTZ19 (Pharmacia). The nucleotide sequence of the amplification product (without primers) is represented, retrospectively, from nucleotide #1850 to nucleotide #2020 inclusive (FIG. 1, SEQ ID NOS 1 and 2). A comparison of the sequence amplified from the human cDNA template with the corresponding region of the rat GluR gene on which the oligonucleotide primers were based revealed only about 60% identity, indicating that a fragment from an unrelated human gene had been identified.

To isolate cDNA coding for the entire human EAA1a receptor, a lambda gt10-based library of human hippocampal cDNA was probed using a PCR-generated, labelled (alpha-$^{32}P$-dCTP) version of the 239 bp amplification product. Of $10^6$ clones screened, probing identified 60 putative clones under the following high stringency hybridization conditions: 6×SSC, 50% formamide, 5% Denhardt's solution, 0.5% SDS, 100 ug/ml denatured salmon sperm DNA. Hybridizations were carried out at 37° C. overnight, and filters were washed with 2×SSC containing 0.5% SDS at 25C for 5 minutes, followed by a 15 minute wash at 50C with 2×SSC containing 0.5% SDS. The final wash was with 1×SSC containing 0.5% SDS at 50C for 15 minutes. Filters were exposed to X-ray film (Kodak) overnight.

Hybridization studies were performed in duplicate, and only those clones which hybridized well in both duplicates were selected for further analysis. Upon second round screening, 50 of the original 60 putative clones were selected. All 50 putative clones were plaque-purified, large scale DNA preps were made, and then DNA inserts liberated therefrom were subcloned into the EcoRI site of pTZ18 vectors, for sequence analysis. Sequencing revealed one clone harbouring, internally, a region with a nucleotide sequence identical to the sequence of the original 239 bp subclone. The entire sequence of the isolated clone (1058 bp) was then determined. Retrospectively, this 1058 bp sub-clone is represented from nucleotide 1245 to nucleotide 2302 inclusive (FIG. 1, SEQ ID NOS 1 and 2).

Figure 3A:
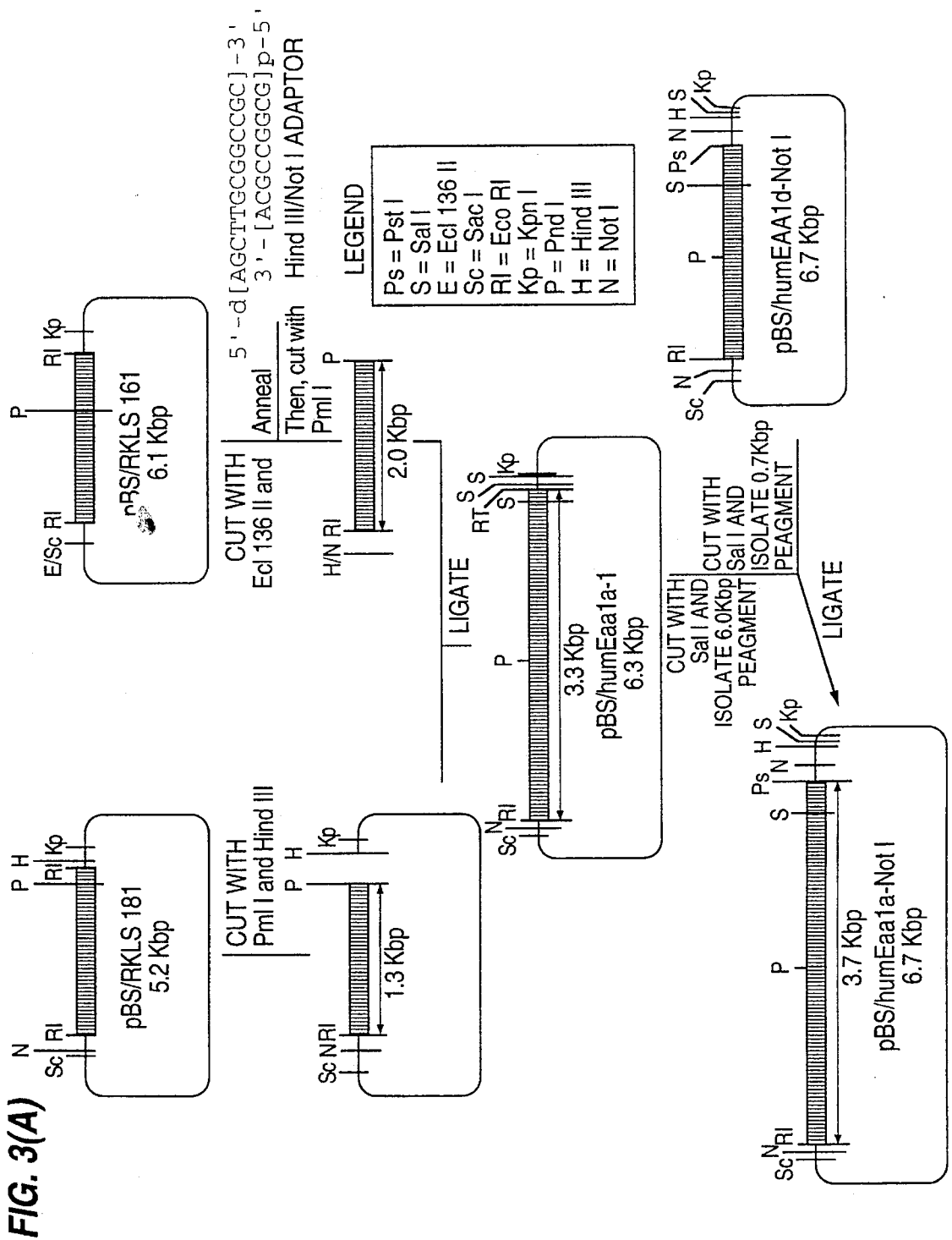

Since it was likely by analogy with the other receptor genes that the 1058 bp was not full length, an alternative human hippocampal cDNA library constructed in a lambda phage system known commercially as lambda ZAP II was obtained (Stratagene Cloning Systems, La Jolla, Calif., U.S.A.) and screened using a PCR-generated, radiolabelled version of the 1058 bp subclone. Screening of $10^6$ clones of this library by hybridization under the stringency conditions detailed above lead initially to the selection of 50 positive clones. For sequencing, phagemids carrying the inserts were excised, to generate insert-carrying variants of the phagemid vector known commercially as Bluescript-SK. Sequencing analysis identified two phagemid clones sharing a sequence overlap. One clone carrying a 2.2 kb EcoRI/EcoRI insert, and apparently representing a 5' region of the open reading frame, was designated pBS/RKLS181. The overlapping clone carrying a 3.1 kb EcoRI/EcoRI insert and appearing to represent the remaining 3' region of the open reading frame, was designated pBS/RKLS 161. To construct the entire open reading frame, the strategy shown in FIG. 3(1) was employed, to generate the phagemid pBS/HumEAA1a which carries the EAA1a-encoding DNA as a 3.7 kb EcoRI/PstI insert (recoverable intact as a 3.7 kb NotI/NotI insert) in a 3.0 kb Bluescript-SK phagemid background. The entire sequence of the EcoRI/PstI insert is provided in FIG. 1 (SEQ ID NOS 1 and 2).

The 6.7 kb phagemid pBS/humEAA1a-NotI was deposited, under the terms of the Budapest Treaty, with the American Type Culture Collection in Rockville, Md. USA on Aug. 21, 1991, and has been assigned accession number ATCC 75063.

EXAMPLE 2

Alternative Strategy For Obtaining EAA1a Receptor-encoding DNA

Having herein provided the nucleotide sequence of EAA1a-encoding DNA, it will be appreciated that isolation thereof by the procedures just described is unnecessary, and can be replaced by application of automated techniques of gene synthesis and amplification. Using an appropriate cDNA library as template, for example a carefully prepared human hippocampal cDNA library, the polymerase chain reaction technique can be applied to amplify the desired cDNA product. While current PCR protocols are unlikely to enable direct amplification of the entire 3.7 kb gene, regional amplification to generate ligatable gene fragments is a feasible approach to gene construction.

Figure 2:
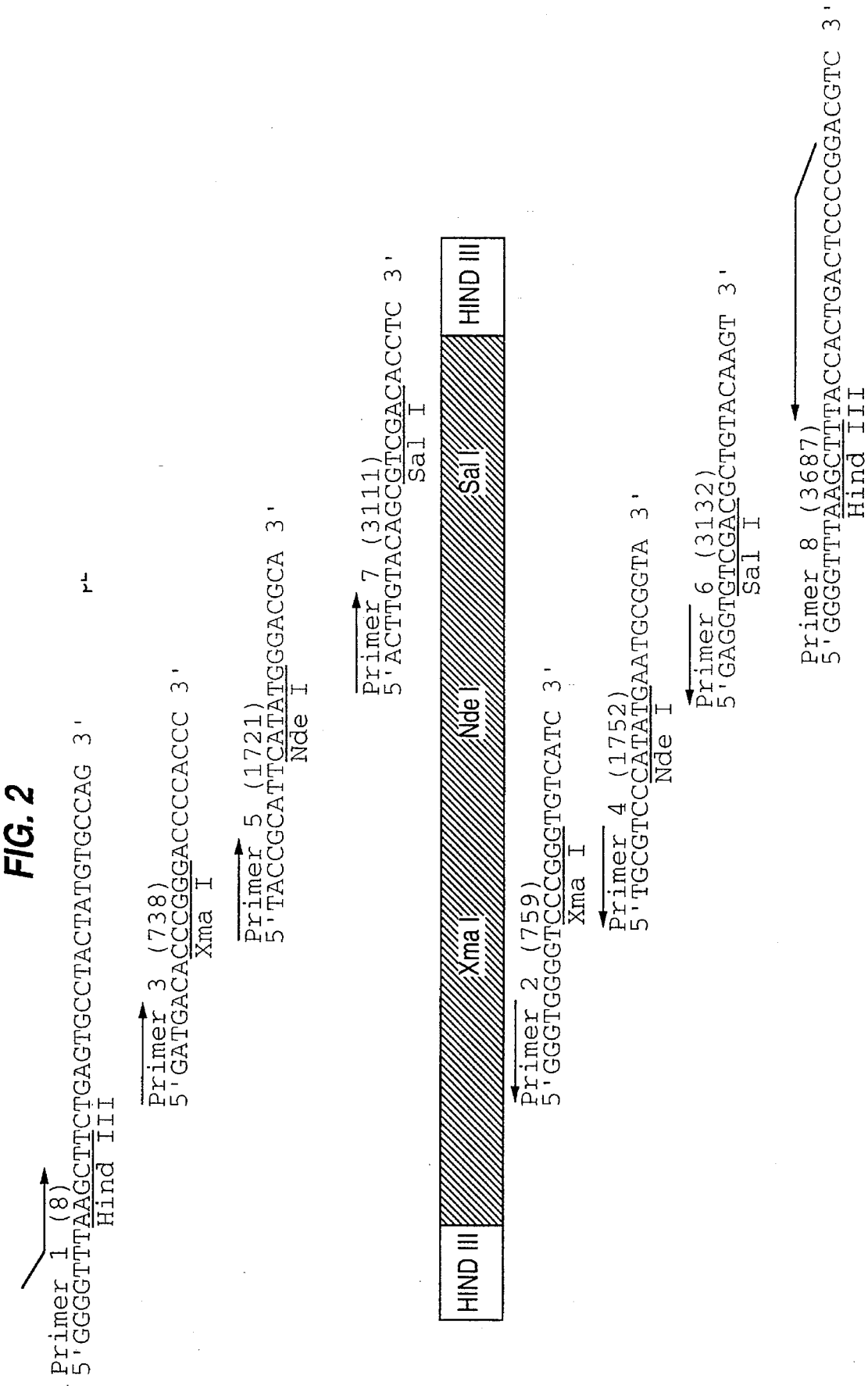

With reference specifically to the EAA1a-encoding DNA, PCR-facilitated gene construction can proceed, for example, as illustrated in FIG. 2 (SEQ ID NOS 3–10). More particularly, regions of the cloned cDNA template are amplified as fragments comprising on the order of several hundred nucleotides, using primers bearing non-hybridizing 5' flanks that constitute restriction sites useful in subsequent steps of gene assembly. In the example illustrated in FIG. 2, the gene is amplified as 4 individual fragments that can be ligated, because of the careful selection of restriction sites, in one step to form the entire EAA1a receptor-encoding DNA.

It will also be appreciated that automated techniques of gene synthesis can be applied, to provide gene fragments that by PCR can be amplified and subsequently ligated. Using current protocols, for example as described by Barnett et al in Nucl. Acids Res., 1990, 18(10):3094, fragments up to about 300 bases in length can be synthesized, and then amplified again using restriction site-tailed primers to facilitate assembly of the de novo synthesized gene regions.

EXAMPLE 3

Construction of Genetically Engineered Cells Producing the Human EAA1a Receptor For transient expression in mammalian cells, cDNA coding for the human EAA1a receptor was incorporated into the mammalian expression vector pcDNA1, which is available commercially from Invitrogen Corporation (San Diego, Calif., USA; catalogue number V490-20). This is a multifunctional 4.2 kb plasmid vector designed for cDNA expression in eukaryotic systems, and cDNA analysis in prokaryotes. Incorporated on the vector are the CMV promoter and enhancer, splice segment and polyadenylation signal, an SV40 and Polyoma virus origin of replication, and M13 origin to rescue single strand DNA for sequencing and mutagenesis, Sp6 and T7 RNA promoters for the production of sense and anti-sense RNA transcripts and a Col E1-like high copy plasmid origin. A polylinker is located appropriately downstream of the CMV promoter (and 3' of the T7 promoter).

For incorporation of the EAA1a receptor-encoding cDNA into an expression vector, the cDNA source insert was released from pBS/hum EAA1a-NotI as a 3.7 kb NotI/NotI fragment, which was then incorporated at the NotI site in the pcDNAI polylinker. Sequencing across the NotI junction was performed, to conform proper insert orientation in pcDNA1. The resulting plasmid, designated pcDNA1/humEAA1a, was then introduced for transient expression into a selected mammalian cell host, in this case the monkey-derived, fibroblast like cells of the COS-1 lineage (available from the American Type Culture. Collection, Rockville, Md. as ATCC CRL 1650).

For transient expression of the EAA1-encoding DNA, COS-1 cells were transfected with approximately 8 ug DNA (as pcDNA1/humEAA1a) per $10^6$ COS cells, by DEAE-mediated DNA transfection and treated with chloroquine according to the procedures described by Maniatis et al, supra. Briefly, COS-1 cells were plated at a density of $5 \times 10^6$ cells/dish and then gown for 24 hours in FBS-supplemented DMEM/F12 medium. Medium was then removed and cells were washed in PBS and then in medium. There was then applied on the cells 10 ml of a transfection solution containing DEAE dextran (0.4 mg/ml), 100 μM chloroquine, 10% NuSerum, DNA (0.4 mg/ml) in DMEM/F12 medium. After incubation for 3 hours at 37C, cells were washed in PBS and medium as just described and then shocked for 1 minute with 10% DMSO in DMEM/F12 medium. Cells were allowed to grow for 2–3 days in 10% FBS-supplemented medium, and at the end of incubation dishes were placed on ice, washed with ice cold PBS and then removed by scraping. Cells were then harvested by centrifugation at 1000 rpm for 10 minutes and the cellular pellet was frozen in liquid nitrogen, for subsequent use in ligand binding assays. Northern blot analysis of a thawed aliquot of frozen cells confirmed expression of receptor-encoding cDNA in cells under storage.

In a like manner, stably transfected cell lines were also prepared using two different cell types as host: CHO K1 and CHO Pro5. To construct these cell lines, cDNA coding for human EAA1a was incorporated into the NotI site of a 7.1 kb derivative of plasmid vector pcDNA1, which incorporates the neomycin gene under control of the Rous Sarcoma Virus LTR promoter and is designated pcDNA1/NEO (available also from Invitrogen Corporation, catalogue #V492-20). In a similar fashion, and again using a convenient NotI site for insertion, the receptor-encoding cDNA was inserted into the mammalian expression vector pRC/CMV (Invitrogen), which enables stable expression. Insertion at this site placed the cDNA under the expression control of the cytomegalovirus promoter and upstream of the polyadenylation site and terminator of the bovine growth hormone gene, and into a vector background comprising the neomycin resistance gene (driven by the SV40 early promoter) as selectable marker.

To introduce plasmids constructed as described above, the host CHO cells were first seeded at a density of $5 \times 10^5$ in 10% FBS-supplemented MEM medium. After growth for 24 hours, fresh medium was added to the plates and three hours later, the cells were transfected using the calcium phosphate-DNA co-precipitation procedure (Maniatis et al, supra). Briefly, 3 ug of DNA was mixed and incubated with buffered calcium solution for 10 minutes at room temperature. An equal volume of buffered phosphate solution was added and the suspension was incubated for 15 minutes at room temperature. Next, the incubated suspension was applied to the cells for 4 hours, removed and cells were shocked with medium containing 15% glycerol. Three minutes later, cells were washed with medium and incubated for 24 hours at normal growth conditions. Cells resistant to neomycin were selected in 10% FBS-supplemented alpha-MEM medium containing G418 (1 mg/ml). Individual colonies of G418-resistant cells were isolated about 2–3 weeks later, clonally selected and then propogated for assay purposes.

EXAMPLE 4

Ligand Binding Assays

Transfected cells in the frozen state were resuspended in ice-cold distilled water using a hand homogenizer and centrifuged for 20 minutes at 50,000 g. The supernatant was discarded and the membrane pellet stored frozen at −70C.

COS cell membrane pellets were suspended in ice cold 50 mM Tris-HCl (pH 7.55, 5C) and placed inside Spectrapor 7 (EDTA-treated, sulfur-free) dialysis tubing. The suspension was placed in 4 liters of ice cold 50 mM Tris-HCl (pH 7.55, 5C) and dialyzed for 16–24 hours at 5C in order to remove endogenous glutamate that would compete for binding. The tissue suspension was recovered from the tubing along with a small volume of buffer used to rinse the tubing. This resultant membrane preparation was used as tissue source for binding experiments described below. Proteins were determined using the Pierce Reagent with BSA as standard.

Binding assays were then performed, using an amount of COS-derived membrane equivalent to from 25–100 ug as judged by protein determination and selected radiolabelled ligand. In particular, glutamate binding assays entailed formation of an incubation mixture consisting of 25–100 ug of tissue protein, and [3,4-3H]L-glutamic acid (47.3 Ci/mmole, 10 nM final) in 50 mM Tris-HCl (pH 7.55, 5C) in 1 ml final volume. Non-specific binding was in the presence of 1 mM L-glutamate. Samples were incubated on ice for 60 minutes in plastic minivials. Bound and free ligand were separated by centrifugation for 10 minutes at 50,000 g (4C). Tissue pellets were washed superficially with 2×6 ml of ice cold incubation buffer. Pellets were solubilized and counted in 5 ml of Beckman Ready Protein Scintillation cocktail.

For kainate binding assays, incubation mixtures consisted of 25–100 ug tissue protein and [vinylidene-3H] kainic acid (58Ci/mmole, 5 nM final) in the cold incubation buffer, 1 ml final volume. Non-specific binding was in the presence of 1 mM L-glutamate. Samples were incubated as for the glutamate binding assays, and bound and free ligand were separated by rapid filtration using a Brandel cell harvester and GF/B filters pre-soaked in ice-cold 0.3% polyethyleneimine. Filters were washed twice in 6 ml of the cold incubation buffer, then placed in scintillation vials with 5 ml of Beckman Ready-Safe scintillation cocktail for counting.

AMPA-binding assays were also performed in substantially the same manner described above for kainate binding, but using as ligand D,L-alpha-[5-methyl-3H]amino-3-hydroxy-5-methylisoxazole-4-propionic acid (3H-AMPA, 27.6Ci/mmole, 5 nM final) with 0.1M KSCN and 2.5 mM CaCl$_2$ in the 1 ml final volume.

Figure 5:
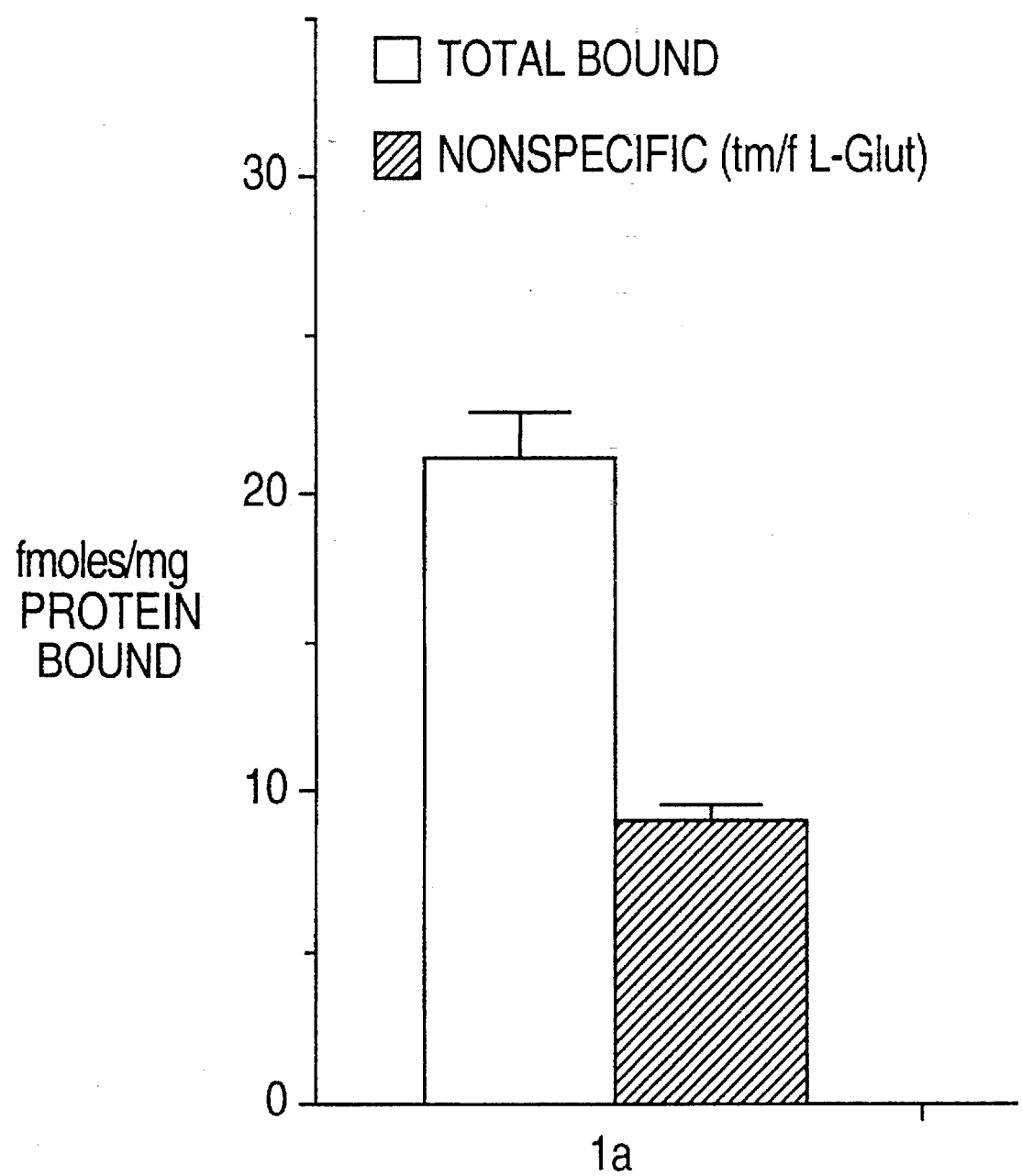

Assays performed in this manner, using membrane preparations derived from the EAA1a-producing COS cells, revealed specific [3H]-kainate binding at 5 nM and [3H]-glutamate binding at 10 nM, labelled ligand (FIG. 5). Mock transfected cells exhibited no specific binding of any of the ligands tested. These results demonstrate clearly that the human EAA1a receptor is binding kainate with high affinity. This activity, coupled with the fact that there is little or no demonstrable binding of either AMPA or NMDA clearly assigns the EAA1a receptor to be of the kainate type of EAA receptor. Furthermore, this binding profile, especially with the kainate binding being of the high affinity category (i.e. nanomolar range) indicates that the receptor is functioning in an authentic manner, and can therefore reliably predict the ligand binding "signature" of its non-recombinant counterpart from the intact human brain. These features make the recombinant receptor especially useful for selecting and characterizing ligand compounds which bind to the receptor, and/or for selecting and characterizing compounds which may act by displacing other ligands from the receptor. The isolation of the EAA1a receptor gene in a pure form, capable of being expressed as a single, homogenous receptor species, therefore frees the ligand binding assay from the lack of precision introduced when complex, heterogeneous receptor preparations from human brains are used to attempt such characterizations.

EXAMPLE 5

Naturally Occurring Variants of the Human EAA1a Receptor

Using the same 1058 bp probe which lead to the successful identification of the human EAA1a receptor, three sequence-related variants thereof were also identified and isolated, in substantially the same manner. As shown in FIG. 4, one variant designated EAA1d (shown partially in SEQ ID NO: 13) is similar in many structural respects to the human EAA1a (shown partially in SEQ ID NO: 14) receptor, and differs only by the precise insertion in EAA1d of an 11 bp insertion, between nucleotide positions 1426 and 1427 of EAA1a. Like DNA coding for EAA1a, the EAA1d-encoding DNA was isolated from a cDNA library of human hippocampal DNA. To construct the full length cDNA containing the entire open reading frame, overlapping clones pBS/RKLS181 (representing the 5'-region) and pBS/RKLS911 (representing the 3'-region) were combined using the strategy shown in FIG. 3(2). For binding studies, the isolated cDNA insert has been released from pBShumEAA1d-NotI, as a 3.7 kb NotI/NotI fragment, and has been introduced for transient expression into cells of the COS-1 lineage after insertion into the vector pcDNA1 and, for stable expression, into CHO K1 or CHO Pro5 cells after insertion into vectors pcDNA1/NEO and pRC/CMV, all in the same manner as described above for human EAA1a.

A plasmid, designated pBS/humEAA1d-NotI, which carries a 3.7 kb NotI/NotI cDNA insert coding for the human EAA1d receptor in a 3.0 kb Bluescript-SK background, has been deposited, under the terms of the Budapest Treaty, with the American Type Culture Collection in Rockville, Md. USA on Aug. 21, 1991, under accession number ATCC 75064.

Another variant uncovered in the human hippocampal cDNA library using the same cloning strategy, designated the human EAA1b (shown partially in SEQ ID NO: 14 ) receptor, is nearly identical in all respects to EAA1a, except for a single nucleotide difference at position #1737 which results in a valine to isoleucine change within the extracellular N-terminal region of EAA1a, as shown in FIG. 4. DNA coding for a third variant designated human EAA1c (shown partially in SEQ iD NO: 15) was also isolated using the herein described cloning strategy and the human hippocampal cDNA library, carries a 24 bp (8 amino acid) deletion relative to EAA1a, in the extracellular N-terminal region thereof (FIG. 4).

5,616,481

We claim:

1. A method of assaying a candidate ligand compound for binding affinity to a human EAA receptor, which comprises the steps of incubating a labelled form of said compound with a cell or with a membrane preparation derived from a cell, said cell having incorporated expressibly therein a heterologous DNA molecule that encodes a human EAA1 receptor selected from the group consisting of:

an EAA1a receptor having the amino acid sequence of residues 1-936 of SEQ ID NO: 2 with a valine residue at amino acid position 508;

an EAA1b receptor having the amino acid sequence of residues 1-936 of SEQ ID NO: 2;

an EAA1c receptor wherein the polynucleotide coding therefor includes nucleotides 216 to 3023 of of SEQ ID NO: 1, or degenerate codon equivalents thereof, in which nucleotides 1427–1450 are deleted and the codon at position 1713 encodes isoleucine; and an EAA1d receptor, wherein the olynucleotide coding therefor includes nucleotides 216–3023 of SEQ ID NO: 1, or degenerate codon equivalents thereof, in which nucleotides 1412–1460 are replaced by SEQ ID NO: 13;

washing unbound ligand compound from the incubation mixture, and then determining the presence of membrane-bound ligand compound.

2. A method as defined in claim 1, wherein said EAA1 receptor is the EAA1a receptor.

3. A method as defined in claim 1, wherein said EAA1 receptor is the EAA1b receptor.

4. A method as defined in claim 1, wherein said EAA1 receptor is the EAA1c receptor.

5. A method as defined in claim 1, wherein said EAA1 receptor is the EAA1d receptor.

6. A method for determining the binding affinity of a candidate ligand compound for a human EAA receptor, which comprises the steps of incubating a cell or a membrane preparation derived from said cell with a labelled EAA receptor ligand to form a ligand/receptor complex, said cell having incorporated expressibly therein a heterologous DNA molecule that encodes a human EAA1 receptor selected from the group consisting of:

an EAA1a receptor having the amino acid sequence of residues 1-936 of SEQ ID NO: 2 with a valine residue at amino acid position 508;

an EAA1b receptor having the amino acid sequence of residues 1-936 of SEQ ID NO: 2;

an EAA1c receptor, wherein the polynucleotide coding therefor includes nucleotides 216 to 3023 of SEQ ID NO: 1 or degenerate codon equivalents thereof, in which nucleotides 1427–1450 are deleted and the codon at position 1713 encodes isoleucine; and an EAA1d receptor, wherein the polynucleotide coding therefor includes nucleotides 216–3023 of SEQ ID NO: 1, or degenerate codon equivalents thereof, in which nucleotides 1412–1460 are replaced by SEQ ID NO: 13;

removing unbound ligand, incubating the receptor/ligand complex with said compound, and measuring the amount of labelled ligand displaced from or remaining in the receptor/ligand complex.

7. A method as defined in claim 6, wherein said EAA1 receptor is the EAA1a receptor.

8. A method as defined in claim 6, wherein said EAA1 receptor is the EAA1b receptor.

9. A method as defined in claim 6, wherein said EAA1 receptor is the EAA1c receptor.

10. A method as defined in claim 6, wherein said EAA1 receptor is the EAA1d receptor.

11. A method of assaying a candidate ligand for binding interaction with a human EAA receptor, which comprises the steps of incubating the candidate ligand under appropriate conditions with a cell or with a membrane preparation derived from a cell, said cell having incorporated expressibly therein a heterologous DNA molecule that encodes a human EAA1 receptor selected from the group consisting of:

an EAA1a receptor having the amino acid sequence of residues 1-936 of SEQ ID NO: 2 with a valine residue at amino acid position 508;

an EAA1b receptor having the amino acid sequence of residues 1-936 of SEQ ID NO: 2;

an EAA1c receptor wherein the polynucleotide coding therefor includes nucleotides 216 to 3023 of SEQ ID NO: 1 or degenerate codon equivalents thereof, in which nucleotides 1427–1450 are deleted and the codon at position 1713 encodes isoleucine; and an EAA1d receptor, wherein the polynucleotide coding therefor includes nucleotides 216–3023 of SEQ ID NO: 1, or degenerate codon equivalents thereof, in which nucleotides 1412–1460 are replaced by SEQ ID NO: 13;

and then determining the interaction between the EAA1 receptor and the candidate ligand electrophysiologically.

12. A method as defined in claim 11, wherein said EAA1 receptor is the EAA1a receptor.

13. A method as defined in claim 11, wherein said EAA1 receptor is the EAA1b receptor.

14. A method as defined in claim 11, wherein said EAA1 receptor is the EAA1c receptor.

15. A method as defined in claim 11, wherein said EAA1 receptor is the EAA1d receptor.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
    ( A ) LENGTH: 3708 base pairs
    ( B ) TYPE: nucleic acid
    ( C ) STRANDEDNESS: double
    ( D ) TOPOLOGY: linear ( i i ) MOLECULE TYPE: cDNA ( i x ) FEATURE:
    ( A ) NAME/KEY: CDS
    ( B ) LOCATION: 156..3026

( i x ) FEATURE:
    ( A ) NAME/KEY: sig_peptide
    ( B ) LOCATION: 156..215

( i x ) FEATURE:
    ( A ) NAME/KEY: mat_peptide
    ( B ) LOCATION: 216..3026

( x i ) SEQUENCE DESCRIPTION: SEQ ID NO:1:

```
GAATTCCCTG AGTGCCTACT ATGTGCCAGC CTGTGCTAGG CACTGAGGAC ACAGGTGGAA        60

AAGCCCGAAT TGCTCCCTGC TCTCCTGGCG CTCATCACCC CGGAGAGTTA TGTCATGCCC       120

AGGCCAGCAG GGGGCTCCAT GAGGATTCAT AGAAG ATG CCC CGC GTC TCG GCG         173
                                      Met Pro Arg Val Ser Ala
                                      -20                   -15

CCT TTG GTG CTG CTT CCT GCG TGG CTC GTG ATG GTC GCC TGC AGC CCG        221
Pro Leu Val Leu Leu Pro Ala Trp Leu Val Met Val Ala Cys Ser Pro
        -10               -5                        1

CAC TCC TTG AGG ATC GCT GCT ATC TTG GAC GAC CCC ATG GAG TGC AGC        269
His Ser Leu Arg Ile Ala Ala Ile Leu Asp Asp Pro Met Glu Cys Ser
         5                  10                  15

AGA GGG GAG CGG CTC TCC ATC ACC CTG GCC AAG AAC CGC ATC AAC CGC        317
Arg Gly Glu Arg Leu Ser Ile Thr Leu Ala Lys Asn Arg Ile Asn Arg
    20                  25                  30

GCT CCT GAG AGG CTG GGC AAG GCC AAG GTC GAA GTG GAC ATC TTT GAG        365
Ala Pro Glu Arg Leu Gly Lys Ala Lys Val Glu Val Asp Ile Phe Glu
35                  40                  45                  50

CTT CTC AGA GAC AGC GAG TAC GAG ACT GCA GAA ACC ATG TGT CAG ATC        413
Leu Leu Arg Asp Ser Glu Tyr Glu Thr Ala Glu Thr Met Cys Gln Ile
                55                  60                  65

CTC CCC AAG GGG GTG GTC GCT GTC CTC GGA CCA TCG TCC AGC CCA GCC        461
Leu Pro Lys Gly Val Val Ala Val Leu Gly Pro Ser Ser Ser Pro Ala
            70                  75                  80

TCC AGC TCC ATC ATC AGC AAC ATC TGT GGA GAG AAG GAG GTC CCT CAC        509
Ser Ser Ser Ile Ile Ser Asn Ile Cys Gly Glu Lys Glu Val Pro His
        85                  90                  95

TTC AAA GTG GCC CCA GAG GAG TTC GTC AAG TTC CAG TTC CAG AGA TTC        557
Phe Lys Val Ala Pro Glu Glu Phe Val Lys Phe Gln Phe Gln Arg Phe
    100                 105                 110

ACA ACC CTG AAC CTC CAC CCC AGC AAC ACT GAC ATC AGC GTG GCT GTA        605
Thr Thr Leu Asn Leu His Pro Ser Asn Thr Asp Ile Ser Val Ala Val
115                 120                 125                 130

GCT GGG ATC CTG AAC TTC TTC AAC TGC ACC ACC GCC TGC CTC ATC TGT        653
Ala Gly Ile Leu Asn Phe Phe Asn Cys Thr Thr Ala Cys Leu Ile Cys
                135                 140                 145
```

-continued

| | | | | | | | | | | | | | | | | |
|---|---|---|---|---|---|---|---|---|---|---|---|---|---|---|---|---|
| GCC | AAA | GCA | GAA | TGC | CTT | TTA | AAC | CTA | GAG | AAG | CTG | CTC | CGG | CAA | TTC | 701 |
| Ala | Lys | Ala | Glu | Cys | Leu | Leu | Asn | Leu | Glu | Lys | Leu | Leu | Arg | Gln | Phe | |
| | | 150 | | | | | | 155 | | | | | 160 | | | |
| CTT | ATC | TCC | AAG | GAC | ACG | CTG | TCC | GTC | CGC | ATG | CTG | GAT | GAC | ACC | CGG | 749 |
| Leu | Ile | Ser | Lys | Asp | Thr | Leu | Ser | Val | Arg | Met | Leu | Asp | Asp | Thr | Arg | |
| | | 165 | | | | | 170 | | | | | 175 | | | | |
| GAC | CCC | ACC | CCG | CTC | CTC | AAG | GAG | ATC | CGG | GAC | GAC | AAG | ACC | GCC | ACC | 797 |
| Asp | Pro | Thr | Pro | Leu | Leu | Lys | Glu | Ile | Arg | Asp | Asp | Lys | Thr | Ala | Thr | |
| | 180 | | | | | 185 | | | | | 190 | | | | | |
| ATC | ATC | ATC | CAC | GCC | AAC | GCC | TCC | ATG | TCC | CAC | ACC | ATC | CTC | CTG | AAG | 845 |
| Ile | Ile | Ile | His | Ala | Asn | Ala | Ser | Met | Ser | His | Thr | Ile | Leu | Leu | Lys | |
| 195 | | | | | 200 | | | | | 205 | | | | | 210 | |
| GCA | GCC | GAA | CTT | GGG | ATG | GTG | TCA | GCC | TAT | TAC | ACA | TAC | ATC | TTC | ACT | 893 |
| Ala | Ala | Glu | Leu | Gly | Met | Val | Ser | Ala | Tyr | Tyr | Thr | Tyr | Ile | Phe | Thr | |
| | | | | 215 | | | | | 220 | | | | | 225 | | |
| AAT | CTG | GAG | TTC | TCA | CTC | CAG | AGA | ACG | GAC | AGC | CTT | GTG | GAT | GAT | CGT | 941 |
| Asn | Leu | Glu | Phe | Ser | Leu | Gln | Arg | Thr | Asp | Ser | Leu | Val | Asp | Asp | Arg | |
| | | | 230 | | | | | 235 | | | | | 240 | | | |
| GTC | AAC | ATC | CTG | GGA | TTT | TCC | ATT | TTC | AAC | CAA | TCC | CAT | GCT | TTC | TTC | 989 |
| Val | Asn | Ile | Leu | Gly | Phe | Ser | Ile | Phe | Asn | Gln | Ser | His | Ala | Phe | Phe | |
| | | 245 | | | | | 250 | | | | | 255 | | | | |
| CAA | GAG | TTT | GCC | CAG | AGC | CTC | AAC | CAG | TCC | TGG | CAG | GAG | AAC | TGT | GAC | 1037 |
| Gln | Glu | Phe | Ala | Gln | Ser | Leu | Asn | Gln | Ser | Trp | Gln | Glu | Asn | Cys | Asp | |
| | 260 | | | | | 265 | | | | | 270 | | | | | |
| CAT | GTG | CCC | TTC | ACT | GGG | CCT | GCG | CTC | TCC | TCG | GCC | CTG | CTG | TTT | GAT | 1085 |
| His | Val | Pro | Phe | Thr | Gly | Pro | Ala | Leu | Ser | Ser | Ala | Leu | Leu | Phe | Asp | |
| 275 | | | | | 280 | | | | | 285 | | | | | 290 | |
| GCT | GTC | TAT | GCT | GTG | GTG | ACT | GCG | GTG | CAG | GAA | CTG | AAC | CGG | AGC | CAA | 1133 |
| Ala | Val | Tyr | Ala | Val | Val | Thr | Ala | Val | Gln | Glu | Leu | Asn | Arg | Ser | Gln | |
| | | | | 295 | | | | | 300 | | | | | 305 | | |
| GAG | ATC | GGC | GTG | AAG | CCC | TTG | TCC | TGC | GGC | TCG | GCC | CAG | ATC | TGG | CAG | 1181 |
| Glu | Ile | Gly | Val | Lys | Pro | Leu | Ser | Cys | Gly | Ser | Ala | Gln | Ile | Trp | Gln | |
| | | | 310 | | | | | 315 | | | | | 320 | | | |
| CAC | GGC | ACC | AGC | CTC | ATG | AAC | TAC | CTG | CGC | ATG | GTA | GAA | TTG | GAA | GGT | 1229 |
| His | Gly | Thr | Ser | Leu | Met | Asn | Tyr | Leu | Arg | Met | Val | Glu | Leu | Glu | Gly | |
| | | 325 | | | | | 330 | | | | | 335 | | | | |
| CTT | ACC | GGC | CAC | ATT | GAA | TTC | AAC | AGC | AAA | GGC | CAG | AGG | TCC | AAC | TAC | 1277 |
| Leu | Thr | Gly | His | Ile | Glu | Phe | Asn | Ser | Lys | Gly | Gln | Arg | Ser | Asn | Tyr | |
| | 340 | | | | | 345 | | | | | 350 | | | | | |
| GCT | TTG | AAA | ATC | TTA | CAG | TTC | ACA | AGG | AAT | GGT | TTT | CGG | CAG | ATC | GGC | 1325 |
| Ala | Leu | Lys | Ile | Leu | Gln | Phe | Thr | Arg | Asn | Gly | Phe | Arg | Gln | Ile | Gly | |
| 355 | | | | | 360 | | | | | 365 | | | | | 370 | |
| CAG | TGG | CAC | GTG | GCA | GAG | GGC | CTC | AGC | ATG | GAC | AGC | CAC | CTC | TAT | GCC | 1373 |
| Gln | Trp | His | Val | Ala | Glu | Gly | Leu | Ser | Met | Asp | Ser | His | Leu | Tyr | Ala | |
| | | | | 375 | | | | | 380 | | | | | 385 | | |
| TCC | AAC | ATC | TCG | GAC | ACT | CTC | TTC | AAC | ACC | ACC | CTG | GTC | GTC | ACC | ACC | 1421 |
| Ser | Asn | Ile | Ser | Asp | Thr | Leu | Phe | Asn | Thr | Thr | Leu | Val | Val | Thr | Thr | |
| | | | 390 | | | | | 395 | | | | | 400 | | | |
| ATC | CTG | GAA | AAC | CCA | TAT | TTA | ATG | CTG | AAG | GGG | AAC | CAC | CAG | GAG | ATG | 1469 |
| Ile | Leu | Glu | Asn | Pro | Tyr | Leu | Met | Leu | Lys | Gly | Asn | His | Gln | Glu | Met | |
| | | 405 | | | | | 410 | | | | | 415 | | | | |
| GAA | GGC | AAT | GAC | CGC | TAC | GAG | GGC | TTC | TGT | GTG | GAC | ATG | CTC | AAG | GAG | 1517 |
| Glu | Gly | Asn | Asp | Arg | Tyr | Glu | Gly | Phe | Cys | Val | Asp | Met | Leu | Lys | Glu | |
| | 420 | | | | | 425 | | | | | 430 | | | | | |
| CTG | GCA | GAG | ATC | CTC | CGA | TTC | AAC | TAC | AAG | ATC | CGC | CTG | GTT | GGG | GAT | 1565 |
| Leu | Ala | Glu | Ile | Leu | Arg | Phe | Asn | Tyr | Lys | Ile | Arg | Leu | Val | Gly | Asp | |
| 435 | | | | | 440 | | | | | 445 | | | | | 450 | |
| GGC | GTG | TAC | GGC | GTT | CCC | GAG | GCC | AAC | GGC | ACC | TGG | ACG | GGA | ATG | GTC | 1613 |
| Gly | Val | Tyr | Gly | Val | Pro | Glu | Ala | Asn | Gly | Thr | Trp | Thr | Gly | Met | Val | |
| | | | | 455 | | | | | 460 | | | | | 465 | | |

| | | | | | | | | | | | | | | | | |
|---|---|---|---|---|---|---|---|---|---|---|---|---|---|---|---|---|
| GGG | GAG | CTG | ATC | GCT | AGG | AAA | GCA | GAT | CTG | GCT | GTG | GCA | GGC | CTC | ACC | 1661 |
| Gly | Glu | Leu | Ile | Ala | Arg | Lys | Ala | Asp | Leu | Ala | Val | Ala | Gly | Leu | Thr | |
| | | | 470 | | | | 475 | | | | | 480 | | | | |
| ATT | ACA | GCT | GAA | CGG | GAG | AAG | GTG | ATT | GAT | TTC | TCT | AAG | CCA | TTC | ATG | 1709 |
| Ile | Thr | Ala | Glu | Arg | Glu | Lys | Val | Ile | Asp | Phe | Ser | Lys | Pro | Phe | Met | |
| | | 485 | | | | 490 | | | | | 495 | | | | | |
| ACT | CTG | GGA | ATT | AGC | ATT | CTT | TAC | CGC | ATT | CAT | ATG | GGA | CGC | AAA | CCC | 1757 |
| Thr | Leu | Gly | Ile | Ser | Ile | Leu | Tyr | Arg | Ile | His | Met | Gly | Arg | Lys | Pro | |
| | | 500 | | | | 505 | | | | | 510 | | | | | |
| GGC | TAT | TTC | TCC | TTC | CTG | GAC | CCA | TTT | TCT | CCG | GGC | GTC | TGG | CTC | TTC | 1805 |
| Gly | Tyr | Phe | Ser | Phe | Leu | Asp | Pro | Phe | Ser | Pro | Gly | Val | Trp | Leu | Phe | |
| 515 | | | | | 520 | | | | | 525 | | | | | 530 | |
| ATG | CTT | CTA | GCC | TAT | CTG | GCC | GTC | AGC | TGT | GTC | CTC | TTC | CTG | GTG | GCT | 1853 |
| Met | Leu | Leu | Ala | Tyr | Leu | Ala | Val | Ser | Cys | Val | Leu | Phe | Leu | Val | Ala | |
| | | | | 535 | | | | | 540 | | | | | 545 | | |
| CGG | TTG | ACG | CCC | TAC | GAG | TGG | TAC | AGC | CCA | CAC | CCA | TGT | GCC | CAG | GGC | 1901 |
| Arg | Leu | Thr | Pro | Tyr | Glu | Trp | Tyr | Ser | Pro | His | Pro | Cys | Ala | Gln | Gly | |
| | | | 550 | | | | | 555 | | | | | 560 | | | |
| CGG | TGC | AAC | CTC | CTG | GTG | AAC | CAG | TAC | TCC | CTG | GGC | AAC | AGC | CTC | TGG | 1949 |
| Arg | Cys | Asn | Leu | Leu | Val | Asn | Gln | Tyr | Ser | Leu | Gly | Asn | Ser | Leu | Trp | |
| | | 565 | | | | | 570 | | | | | 575 | | | | |
| TTT | CCG | GTC | GGG | GGG | TTC | ATG | CAG | CAG | GGC | TCC | ACC | ATC | GCC | CCT | CGC | 1997 |
| Phe | Pro | Val | Gly | Gly | Phe | Met | Gln | Gln | Gly | Ser | Thr | Ile | Ala | Pro | Arg | |
| | 580 | | | | | 585 | | | | | 590 | | | | | |
| GCC | TTA | TCC | ACC | CGC | TGT | GTC | AGT | GGC | GTC | TGG | TGG | GCA | TTC | ACG | CTG | 2045 |
| Ala | Leu | Ser | Thr | Arg | Cys | Val | Ser | Gly | Val | Trp | Trp | Ala | Phe | Thr | Leu | |
| 595 | | | | | 600 | | | | | 605 | | | | | 610 | |
| ATC | ATC | ATC | TCA | TCC | TAC | ACG | GCC | AAC | CTG | GCA | GCC | TTC | CTG | ACC | GTG | 2093 |
| Ile | Ile | Ile | Ser | Ser | Tyr | Thr | Ala | Asn | Leu | Ala | Ala | Phe | Leu | Thr | Val | |
| | | | | 615 | | | | | 620 | | | | | 625 | | |
| CAG | CGC | ATG | GAT | GTG | CCC | ATT | GAG | TCA | GTG | GAT | GAC | CTG | GCT | GAC | CAG | 2141 |
| Gln | Arg | Met | Asp | Val | Pro | Ile | Glu | Ser | Val | Asp | Asp | Leu | Ala | Asp | Gln | |
| | | | 630 | | | | | 635 | | | | | 640 | | | |
| ACC | GCC | ATT | GAA | TAT | GGC | ACA | ATT | CAC | GGA | GGC | TCC | AGC | ATG | ACC | TTC | 2189 |
| Thr | Ala | Ile | Glu | Tyr | Gly | Thr | Ile | His | Gly | Gly | Ser | Ser | Met | Thr | Phe | |
| | | 645 | | | | | 650 | | | | | 655 | | | | |
| TTC | CAA | AAT | TCC | CGC | TAC | CAG | ACC | TAC | CAA | CGC | ATG | TGG | AAT | TAC | ATG | 2237 |
| Phe | Gln | Asn | Ser | Arg | Tyr | Gln | Thr | Tyr | Gln | Arg | Met | Trp | Asn | Tyr | Met | |
| | 660 | | | | | 665 | | | | | 670 | | | | | |
| TAT | TCC | AAG | CAG | CCC | AGC | GTG | TTC | GTG | AAG | AGC | ACA | GAG | GAG | GGA | ATC | 2285 |
| Tyr | Ser | Lys | Gln | Pro | Ser | Val | Phe | Val | Lys | Ser | Thr | Glu | Glu | Gly | Ile | |
| 675 | | | | | 680 | | | | | 685 | | | | | 690 | |
| GCC | AGG | GTG | TTG | AAT | TCC | AAC | TAC | GCC | TTC | CTC | CTG | GAA | TCC | ACC | ATG | 2333 |
| Ala | Arg | Val | Leu | Asn | Ser | Asn | Tyr | Ala | Phe | Leu | Leu | Glu | Ser | Thr | Met | |
| | | | | 695 | | | | | 700 | | | | | 705 | | |
| AAC | GAG | TAC | TAT | CGG | CAG | CGA | AAC | TGC | AAC | CTC | ACT | CAG | ATT | GGG | GGC | 2381 |
| Asn | Glu | Tyr | Tyr | Arg | Gln | Arg | Asn | Cys | Asn | Leu | Thr | Gln | Ile | Gly | Gly | |
| | | | 710 | | | | | 715 | | | | | 720 | | | |
| CTG | CTG | GAC | ACC | AAG | GGC | TAT | GGG | ATT | GGC | ATG | CCA | GTC | GGC | TCG | GTT | 2429 |
| Leu | Leu | Asp | Thr | Lys | Gly | Tyr | Gly | Ile | Gly | Met | Pro | Val | Gly | Ser | Val | |
| | | | 725 | | | | | 730 | | | | | 735 | | | |
| TTC | CGG | GAC | GAG | TTT | GAT | CTG | GCC | ATT | CTC | CAG | CTG | CAG | GAG | AAC | AAC | 2477 |
| Phe | Arg | Asp | Glu | Phe | Asp | Leu | Ala | Ile | Leu | Gln | Leu | Gln | Glu | Asn | Asn | |
| | 740 | | | | | 745 | | | | | 750 | | | | | |
| CGC | CTG | GAG | ATC | CTG | AAG | CGC | AAA | TGG | TGG | GAA | GGA | GGG | AAG | TGC | CCC | 2525 |
| Arg | Leu | Glu | Ile | Leu | Lys | Arg | Lys | Trp | Trp | Glu | Gly | Gly | Lys | Cys | Pro | |
| 755 | | | | | 760 | | | | | 765 | | | | | 770 | |
| AAG | GAG | GAA | GAT | CAC | AGA | GCT | AAA | GGC | CTG | GGA | ATG | GAG | AAT | ATT | GGT | 2573 |
| Lys | Glu | Glu | Asp | His | Arg | Ala | Lys | Gly | Leu | Gly | Met | Glu | Asn | Ile | Gly | |
| | | | | 775 | | | | | 780 | | | | | 785 | | |

| | | | | | | | | | | | | | | | | |
|---|---|---|---|---|---|---|---|---|---|---|---|---|---|---|---|---|
| GGA | ATC | TTT | GTG | GTT | CTT | ATT | TGT | GGC | TTA | ATC | GTG | GCC | ATT | TTT | ATG | 2621 |
| Gly | Ile | Phe | Val | Val | Leu | Ile | Cys | Gly | Leu | Ile | Val | Ala | Ile | Phe | Met | |
| | | | 790 | | | | 795 | | | | | | 800 | | | |
| GCT | ATG | TTG | GAG | TTT | TTA | TGG | ACT | CTC | AGA | CAC | TCA | GAA | GCA | ACT | GAG | 2669 |
| Ala | Met | Leu | Glu | Phe | Leu | Trp | Thr | Leu | Arg | His | Ser | Glu | Ala | Thr | Glu | |
| | | 805 | | | | | 810 | | | | | 815 | | | | |
| GTG | TCC | GTC | TGC | CAG | GAG | ATG | GTG | ACC | GAG | CTG | CGC | AGC | ATT | ATC | CTG | 2717 |
| Val | Ser | Val | Cys | Gln | Glu | Met | Val | Thr | Glu | Leu | Arg | Ser | Ile | Ile | Leu | |
| | 820 | | | | | 825 | | | | | 830 | | | | | |
| TGT | CAG | GAC | AGT | ATC | CAC | CCC | CGC | CGG | CGG | CGC | GCC | GCA | GTC | CCG | CCG | 2765 |
| Cys | Gln | Asp | Ser | Ile | His | Pro | Arg | Arg | Arg | Arg | Ala | Ala | Val | Pro | Pro | |
| 835 | | | | | 840 | | | | | 845 | | | | | 850 | |
| CCC | CGG | CCC | CCC | ATC | CCC | GAG | GAG | CGC | CGA | CCG | CGG | GGC | ACG | GCG | ACG | 2813 |
| Pro | Arg | Pro | Pro | Ile | Pro | Glu | Glu | Arg | Arg | Pro | Arg | Gly | Thr | Ala | Thr | |
| | | | | 855 | | | | 860 | | | | | | 865 | | |
| CTC | AGC | AAC | GGG | AAG | CTG | TGC | GGG | GCA | GGG | GAG | CCC | GAC | CAG | CTC | GCG | 2861 |
| Leu | Ser | Asn | Gly | Lys | Leu | Cys | Gly | Ala | Gly | Glu | Pro | Asp | Gln | Leu | Ala | |
| | | | 870 | | | | | 875 | | | | | 880 | | | |
| CAG | AGA | CTG | GCG | CAG | GAG | GCC | GCC | CTG | GTG | GCC | CGC | GGC | TGC | ACG | CAC | 2909 |
| Gln | Arg | Leu | Ala | Gln | Glu | Ala | Ala | Leu | Val | Ala | Arg | Gly | Cys | Thr | His | |
| | | 885 | | | | | 890 | | | | | 895 | | | | |
| ATC | CGC | GTC | TGC | CCC | GAG | TGC | CGC | CGC | TTC | CAG | GGC | CTG | CGG | GCA | CGG | 2957 |
| Ile | Arg | Val | Cys | Pro | Glu | Cys | Arg | Arg | Phe | Gln | Gly | Leu | Arg | Ala | Arg | |
| | 900 | | | | | 905 | | | | | 910 | | | | | |
| CCG | TCG | CCC | GCC | CGC | AGC | GAG | GAG | AGC | CTG | GAG | TGG | GAG | AAA | ACC | ACC | 3005 |
| Pro | Ser | Pro | Ala | Arg | Ser | Glu | Glu | Ser | Leu | Glu | Trp | Glu | Lys | Thr | Thr | |
| 915 | | | | | 920 | | | | | 925 | | | | | 930 | |
| AAC | AGC | AGC | GAG | CCC | GAG | TAGTCCCGGA | | GGCCACAGGA | | CGCGCAGAGG | | | | | | 3053 |
| Asn | Ser | Ser | Glu | Pro | Glu | | | | | | | | | | | |
| | | | | 935 | | | | | | | | | | | | |

| | | | | |
|---|---|---|---|---|
| CCGGGCGGGG | CGGGAGGGGA | GGGGCGGGGC | GGGCGCTGCT | GTCAGCCGCC AGCCGGAACT | 3113 |
| TGTACAGCGT | CGACACCTCT | CCAGATTTCG | GATCCAGTCA | CTTTTCAAAA AGATCAAGGA | 3173 |
| GCCTGACGCC | CCAGCCAGAG | ACCGCGCCCG | GTCAGGGAGC | AGGGTCCACC CGGAAACGTT | 3233 |
| GCACCCAAAG | GGCAAAGGAC | GGCCCTCCCT | CCTGGGCACA | AGGACCCATC TTCTCCCAGT | 3293 |
| GGGTCTTTCC | CTCTCGCCAA | AATAACAAGA | GTATAGGGTG | GGGGTCCCT ACCCAGACCA | 3353 |
| GTCCAATGAA | TTGGTGGAAT | CATCAGTTGA | ATTTCCCCCT | AGTCAGGGGC CAATGTACCC | 3413 |
| TCCGTCTAGT | TCTTACAGAA | AAAAAAAAA | ATTAAACAGG | GAAGTTTTC TTTTCTGGAT | 3473 |
| TTGTATATTT | TTGTTAATGT | TCTTTTCCCT | TTTCTTTCCT | CCTCTCCTTT TCTTCTTTGT | 3533 |
| CATCTTCTCA | GTCCTGTTAA | TTTGTTTTGT | GTTTTTTGGA | GGGGGAGGCT GGGTTAGGGA | 3593 |
| ATGGAAGCCT | AAATAATCCC | TATTTCTTCT | TTTTCCTGAA | TTTTGGAATA TTGCGTTACC | 3653 |
| AGTGCATCCG | ATTTCAGGTG | CGGAACTCTC | TGTATGGTGA | CTGAGGGGCC TGCAG | 3708 |

( 2 ) INFORMATION FOR SEQ ID NO:2:

( i ) SEQUENCE CHARACTERISTICS:
        ( A ) LENGTH: 956 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Pro | Arg | Val | Ser | Ala | Pro | Leu | Val | Leu | Leu | Pro | Ala | Trp | Leu | Val |
| -20 | | | | | -15 | | | | | -10 | | | | | -5 |
| Met | Val | Ala | Cys | Ser | Pro | His | Ser | Leu | Arg | Ile | Ala | Ala | Ile | Leu | Asp |
| | 1 | | | | | 5 | | | | | | | 10 | | |

| | | | | | | | | | | | | | | |
|---|---|---|---|---|---|---|---|---|---|---|---|---|---|---|
| Asp | Pro | Met | Glu | Cys | Ser | Arg | Gly | Glu | Arg | Leu | Ser | Ile | Thr | Leu | Ala |
| | | 15 | | | | 20 | | | | 25 | | | | |
| Lys | Asn | Arg | Ile | Asn | Arg | Ala | Pro | Glu | Arg | Leu | Gly | Lys | Ala | Lys | Val |
| | 30 | | | | 35 | | | | | 40 | | | | |
| Glu | Val | Asp | Ile | Phe | Glu | Leu | Leu | Arg | Asp | Ser | Glu | Tyr | Glu | Thr | Ala |
| 45 | | | | | 50 | | | | 55 | | | | | | 60 |
| Glu | Thr | Met | Cys | Gln | Ile | Leu | Pro | Lys | Gly | Val | Val | Ala | Val | Leu | Gly |
| | | | | 65 | | | | | 70 | | | | | 75 | |
| Pro | Ser | Ser | Ser | Pro | Ala | Ser | Ser | Ser | Ile | Ile | Ser | Asn | Ile | Cys | Gly |
| | | | 80 | | | | | 85 | | | | | 90 | | |
| Glu | Lys | Glu | Val | Pro | His | Phe | Lys | Val | Ala | Pro | Glu | Glu | Phe | Val | Lys |
| | | 95 | | | | 100 | | | | | 105 | | | | |
| Phe | Gln | Phe | Gln | Arg | Phe | Thr | Thr | Leu | Asn | Leu | His | Pro | Ser | Asn | Thr |
| | 110 | | | | | 115 | | | | | 120 | | | | |
| Asp | Ile | Ser | Val | Ala | Val | Ala | Gly | Ile | Leu | Asn | Phe | Phe | Asn | Cys | Thr |
| 125 | | | | | 130 | | | | | 135 | | | | | 140 |
| Thr | Ala | Cys | Leu | Ile | Cys | Ala | Lys | Ala | Glu | Cys | Leu | Leu | Asn | Leu | Glu |
| | | | | 145 | | | | | 150 | | | | | 155 | |
| Lys | Leu | Leu | Arg | Gln | Phe | Leu | Ile | Ser | Lys | Asp | Thr | Leu | Ser | Val | Arg |
| | | | 160 | | | | | 165 | | | | | 170 | | |
| Met | Leu | Asp | Asp | Thr | Arg | Asp | Pro | Thr | Pro | Leu | Leu | Lys | Glu | Ile | Arg |
| | | 175 | | | | | 180 | | | | | 185 | | | |
| Asp | Asp | Lys | Thr | Ala | Thr | Ile | Ile | Ile | His | Ala | Asn | Ala | Ser | Met | Ser |
| | 190 | | | | | 195 | | | | | 200 | | | | |
| His | Thr | Ile | Leu | Leu | Lys | Ala | Ala | Glu | Leu | Gly | Met | Val | Ser | Ala | Tyr |
| 205 | | | | | 210 | | | | | 215 | | | | | 220 |
| Tyr | Thr | Tyr | Ile | Phe | Thr | Asn | Leu | Glu | Phe | Ser | Leu | Gln | Arg | Thr | Asp |
| | | | | 225 | | | | | 230 | | | | | 235 | |
| Ser | Leu | Val | Asp | Asp | Arg | Val | Asn | Ile | Leu | Gly | Phe | Ser | Ile | Phe | Asn |
| | | | 240 | | | | | 245 | | | | | 250 | | |
| Gln | Ser | His | Ala | Phe | Phe | Gln | Glu | Phe | Ala | Gln | Ser | Leu | Asn | Gln | Ser |
| | | 255 | | | | | 260 | | | | | 265 | | | |
| Trp | Gln | Glu | Asn | Cys | Asp | His | Val | Pro | Phe | Thr | Gly | Pro | Ala | Leu | Ser |
| | 270 | | | | | 275 | | | | | 280 | | | | |
| Ser | Ala | Leu | Leu | Phe | Asp | Ala | Val | Tyr | Ala | Val | Val | Thr | Ala | Val | Gln |
| 285 | | | | | 290 | | | | | 295 | | | | | 300 |
| Glu | Leu | Asn | Arg | Ser | Gln | Glu | Ile | Gly | Val | Lys | Pro | Leu | Ser | Cys | Gly |
| | | | | 305 | | | | | 310 | | | | | 315 | |
| Ser | Ala | Gln | Ile | Trp | Gln | His | Gly | Thr | Ser | Leu | Met | Asn | Tyr | Leu | Arg |
| | | | 320 | | | | | 325 | | | | | 330 | | |
| Met | Val | Glu | Leu | Glu | Gly | Leu | Thr | Gly | His | Ile | Glu | Phe | Asn | Ser | Lys |
| | | 335 | | | | | 340 | | | | | 345 | | | |
| Gly | Gln | Arg | Ser | Asn | Tyr | Ala | Leu | Lys | Ile | Leu | Gln | Phe | Thr | Arg | Asn |
| | 350 | | | | | 355 | | | | | 360 | | | | |
| Gly | Phe | Arg | Gln | Ile | Gly | Gln | Trp | His | Val | Ala | Glu | Gly | Leu | Ser | Met |
| 365 | | | | | 370 | | | | | 375 | | | | | 380 |
| Asp | Ser | His | Leu | Tyr | Ala | Ser | Asn | Ile | Ser | Asp | Thr | Leu | Phe | Asn | Thr |
| | | | | 385 | | | | | 390 | | | | | 395 | |
| Thr | Leu | Val | Val | Thr | Thr | Ile | Leu | Glu | Asn | Pro | Tyr | Leu | Met | Leu | Lys |
| | | | 400 | | | | | 405 | | | | | 410 | | |
| Gly | Asn | His | Gln | Glu | Met | Glu | Gly | Asn | Asp | Arg | Tyr | Glu | Gly | Phe | Cys |
| | | 415 | | | | | 420 | | | | | 425 | | | |
| Val | Asp | Met | Leu | Lys | Glu | Leu | Ala | Glu | Ile | Leu | Arg | Phe | Asn | Tyr | Lys |
| | 430 | | | | | 435 | | | | | 440 | | | | |

```
Ile Arg Leu Val Gly Asp Gly Val Tyr Gly Val Pro Glu Ala Asn Gly
445                 450                 455                 460

Thr Trp Thr Gly Met Val Gly Glu Leu Ile Ala Arg Lys Ala Asp Leu
                465                 470                 475

Ala Val Ala Gly Leu Thr Ile Thr Ala Glu Arg Glu Lys Val Ile Asp
            480                 485                 490

Phe Ser Lys Pro Phe Met Thr Leu Gly Ile Ser Ile Leu Tyr Arg Ile
        495                 500                 505

His Met Gly Arg Lys Pro Gly Tyr Phe Ser Phe Leu Asp Pro Phe Ser
    510                 515                 520

Pro Gly Val Trp Leu Phe Met Leu Leu Ala Tyr Leu Ala Val Ser Cys
525                 530                 535                 540

Val Leu Phe Leu Val Ala Arg Leu Thr Pro Tyr Glu Trp Tyr Ser Pro
            545                 550                 555

His Pro Cys Ala Gln Gly Arg Cys Asn Leu Leu Val Asn Gln Tyr Ser
            560                 565                 570

Leu Gly Asn Ser Leu Trp Phe Pro Val Gly Gly Phe Met Gln Gln Gly
        575                 580                 585

Ser Thr Ile Ala Pro Arg Ala Leu Ser Thr Arg Cys Val Ser Gly Val
    590                 595                 600

Trp Trp Ala Phe Thr Leu Ile Ile Ile Ser Ser Tyr Thr Ala Asn Leu
605                 610                 615                 620

Ala Ala Phe Leu Thr Val Gln Arg Met Asp Val Pro Ile Glu Ser Val
            625                 630                 635

Asp Asp Leu Ala Asp Gln Thr Ala Ile Glu Tyr Gly Thr Ile His Gly
            640                 645                 650

Gly Ser Ser Met Thr Phe Phe Gln Asn Ser Arg Tyr Gln Thr Tyr Gln
        655                 660                 665

Arg Met Trp Asn Tyr Met Tyr Ser Lys Gln Pro Ser Val Phe Val Lys
    670                 675                 680

Ser Thr Glu Glu Gly Ile Ala Arg Val Leu Asn Ser Asn Tyr Ala Phe
685                 690                 695                 700

Leu Leu Glu Ser Thr Met Asn Glu Tyr Tyr Arg Gln Arg Asn Cys Asn
            705                 710                 715

Leu Thr Gln Ile Gly Gly Leu Leu Asp Thr Lys Gly Tyr Gly Ile Gly
            720                 725                 730

Met Pro Val Gly Ser Val Phe Arg Asp Glu Phe Asp Leu Ala Ile Leu
    735                 740                 745

Gln Leu Gln Glu Asn Asn Arg Leu Glu Ile Leu Lys Arg Lys Trp Trp
    750                 755                 760

Glu Gly Gly Lys Cys Pro Lys Glu Glu Asp His Arg Ala Lys Gly Leu
765                 770                 775                 780

Gly Met Glu Asn Ile Gly Gly Ile Phe Val Val Leu Ile Cys Gly Leu
            785                 790                 795

Ile Val Ala Ile Phe Met Ala Met Leu Glu Phe Leu Trp Thr Leu Arg
            800                 805                 810

His Ser Glu Ala Thr Glu Val Ser Val Cys Gln Glu Met Val Thr Glu
    815                 820                 825

Leu Arg Ser Ile Ile Leu Cys Gln Asp Ser Ile His Pro Arg Arg Arg
    830                 835                 840

Arg Ala Ala Val Pro Pro Pro Arg Pro Pro Ile Pro Glu Glu Arg Arg
845                 850                 855                 860

Pro Arg Gly Thr Ala Thr Leu Ser Asn Gly Lys Leu Cys Gly Ala Gly
```

|     |     |     |     |     | 865 |     |     |     |     | 870 |     |     |     |     | 875 |     |
|-----|-----|-----|-----|-----|-----|-----|-----|-----|-----|-----|-----|-----|-----|-----|-----|-----|
| Glu | Pro | Asp | Gln | Leu | Ala | Gln | Arg | Leu | Ala | Gln | Glu | Ala | Ala | Leu | Val |     |
|     |     |     | 880 |     |     |     |     | 885 |     |     |     |     | 890 |     |     |     |

Ala Arg Gly Cys Thr His Ile Arg Val Cys Pro Glu Cys Arg Arg Phe
       895              900              905

Gln Gly Leu Arg Ala Arg Pro Ser Pro Ala Arg Ser Glu Glu Ser Leu
    910              915              920

Glu Trp Glu Lys Thr Thr Asn Ser Ser Glu Pro Glu
925              930              935

(2) INFORMATION FOR SEQ ID NO:3:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (xi) SEQUENCE DESCRIPTION: SEQ ID NO:3:

GGGGTTTAAG CTTCTGAGTG CCTACTATGT GCCCAG    36

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (xi) SEQUENCE DESCRIPTION: SEQ ID NO:4:

GGGTGGGGTC CCGGGTGTCA TC    22

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (xi) SEQUENCE DESCRIPTION: SEQ ID NO:5:

GATGACACCC GGGACCCCAC CC    22

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (xi) SEQUENCE DESCRIPTION: SEQ ID NO:6:

TGCGTCCCAT ATGAATGCGG TA    22

(2) INFORMATION FOR SEQ ID NO:7:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( x i ) SEQUENCE DESCRIPTION: SEQ ID NO:7:

TACCGCATTC ATATGGGACG CA 22

( 2 ) INFORMATION FOR SEQ ID NO:8:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( x i ) SEQUENCE DESCRIPTION: SEQ ID NO:8:

GAGGTGTCGA CGCTGTACAA GT 22

( 2 ) INFORMATION FOR SEQ ID NO:9:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( x i ) SEQUENCE DESCRIPTION: SEQ ID NO:9:

ACTTGTACAG CGTCGACACC TC 22

( 2 ) INFORMATION FOR SEQ ID NO:10:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( x i ) SEQUENCE DESCRIPTION: SEQ ID NO:10:

GGGGTTTAAG CTTTACCACT GACTCCCCGG ACGTC 35

( 2 ) INFORMATION FOR SEQ ID NO:11:

( i ) SEQUENCE CHARACTERISTICS:
    ( A ) LENGTH: 13 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( x i ) SEQUENCE DESCRIPTION: SEQ ID NO:11:

AGCTTGCGGC CGC 13

( 2 ) INFORMATION FOR SEQ ID NO:12:

( i ) SEQUENCE CHARACTERISTICS:
  ( A ) LENGTH: 9 base pairs
  ( B ) TYPE: nucleic acid
  ( C ) STRANDEDNESS: single
  ( D ) TOPOLOGY: linear ( i i ) MOLECULE TYPE: Other nucleic acid;
  ( A ) DESCRIPTION: Synthetic DNA oligonucleotide ( i v ) ANTI-SENSE: YES ( x i ) SEQUENCE DESCRIPTION: SEQ ID NO:12:

GCGGCCGCA                                                                                                9

( 2 ) INFORMATION FOR SEQ ID NO:13:

( i ) SEQUENCE CHARACTERISTICS:
    ( A ) LENGTH: 60 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:13:

CGTCACCACC ATCCTGTTTT GCTGCAGGAA AACCCATATT TAATGCTGAA GGGGAACCAC            60

( 2 ) INFORMATION FOR SEQ ID NO:14:

( i ) SEQUENCE CHARACTERISTICS:
    ( A ) LENGTH: 49 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:14:

CGTCACCACC ATCCTGGAAA ACCCATATTT AATGCTGAAG GGGAACCAC                        49

( 2 ) INFORMATION FOR SEQ ID NO:15:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:15:

CGTCACCACC ATCCTGGGGA ACCAC                                                  25

( 2 ) INFORMATION FOR SEQ ID NO:16:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( x i ) SEQUENCE DESCRIPTION: SEQ ID NO:16:

GGGGTTTAAG CTTGAGCGTC GTCCTCTTCC TGGT                                        34

( 2 ) INFORMATION FOR SEQ ID NO:17:

( i ) SEQUENCE CHARACTERISTICS:
  ( A ) LENGTH: 34 base pairs
  ( B ) TYPE: nucleic acid
  ( C ) STRANDEDNESS: single
  ( D ) TOPOLOGY: linear ( i i ) MOLECULE TYPE: Other nucleic acid;
  ( A ) DESCRIPTION: Synthetic DNA oligonucleotide ( x i ) SEQUENCE DESCRIPTION: SEQ ID NO:17:

GGGGTTTAAG CTTGTGAAGA ACCACCAGAC GCCG    34